United States Patent
Middendorf et al.

(10) Patent No.: US 6,207,421 B1
(45) Date of Patent: Mar. 27, 2001

(54) DNA SEQUENCING AND DNA TERMINATORS

(75) Inventors: Lyle Richard Middendorf; John A. Brumbaugh, both of Lincoln, NE (US)

(73) Assignee: Li-Cor, Inc., Lincoln, NE (US)

(*) Notice: Subject to any disclaimer, the term of this patent is extended or adjusted under 35 U.S.C. 154(b) by 0 days.

(21) Appl. No.: 08/505,072

(22) Filed: Jul. 21, 1995

Related U.S. Application Data

(60) Continuation-in-part of application No. 08/275,232, filed on Jul. 14, 1994, now abandoned, which is a division of application No. 07/950,734, filed on Sep. 24, 1989, now Pat. No. 5,346,603, which is a continuation of application No. 07/799,712, filed on Nov. 6, 1991, now abandoned, which is a continuation of application No. 07/632,605, filed on Dec. 24, 1990, now abandoned, which is a continuation of application No. 07/078,279, filed on Jul. 27, 1987, now abandoned, which is a division of application No. 06/594,676, filed on Mar. 29, 1984, now Pat. No. 4,729,947, which is a continuation-in-part of application No. 08/288,461, filed on Aug. 10, 1994, now Pat. No. 5,534,125, which is a division of application No. 08/018,806, filed on Feb. 17, 1993, now Pat. No. 5,360,523, which is a division of application No. 07/763,230, filed on Sep. 20, 1991, now Pat. No. 5,230,781, and a division of application No. 07/570,503, filed on Aug. 21, 1990, now Pat. No. 5,207,880, which is a continuation-in-part of application No. 07/078,279, filed on Jul. 27, 1987, which is a division of application No. 06/594,676, filed on Mar. 29, 1984, now Pat. No. 4,729,947, and a continuation-in-part of application No. 08/204,627, filed on Mar. 1, 1994, now Pat. No. 5,571,388, which is a continuation-in-part of application No. 07/860,140, filed on Mar. 30, 1992, now Pat. No. 5,366,603, which is a division of application No. 07/763,230, filed on Sep. 20, 1991, now Pat. No. 5,230,781, which is a continuation-in-part of application No. 07/570,503, filed on Aug. 21, 1990, now Pat. No. 5,207,880, which is a continuation-in-part of application No. 07/078,279, filed on Jul. 27, 1987, which is a division of application No. 06/594,676, filed on Mar. 29, 1984, now Pat. No. 4,729,947.

(51) Int. Cl.[7] .............................. C12Q 1/68; C12P 19/34; C07H 19/00; C07H 21/00

(52) U.S. Cl. ........................ 435/91.1; 435/6; 435/91.2; 536/22.1; 536/25.3; 536/25.32

(58) Field of Search .......................... 435/6, 91.1, 91.2; 536/22.1, 25.3, 25.32

(56) References Cited

U.S. PATENT DOCUMENTS 3,423,207   1/1969   Heseltine et al. .................. 96/84

(List continued on next page.)

FOREIGN PATENT DOCUMENTS 669003   1/1963   (BE).

(List continued on next page.)

OTHER PUBLICATIONS

Sanger et al. "DNA sequencing with chain–terminating inhibitors" Proc. Natl. Acad. Sci. USA, vol. 74, pp. 5463–5467, Dec. 1977.*

(List continued on next page.)

Primary Examiner—Jezia Riley
(74) Attorney, Agent, or Firm—Vincent L. Carney

(57) ABSTRACT

A universal terminator includes a heterocycle other than naturally occuring DNA heterocycles such as adenine, cytosine, guanine and thymine. In terminating strand synthesis, the hybridized primer-template is split into four aliquots. In the "A" vial is added DNA polymerase and normal amounts of "C", "G", and "T" deoxynucleotides, along with a reduced amount of "A" deoxynucleotide and an amount of the universal terminator such that statistically the universal terminator has less than a one percent chance of being incorporated at sites where a "C", "G", or "T" deoxynucleotide should be incorporated and about a one percent chance of being incorporated at sites where an "A" deoxynucleotide should be incorporated. Similar strategies are followed for the "C", "G", and "T" vials, except that the amount of "C", "G" and "T" deoxynucleotides are reduced for their respective vial.

3 Claims, 13 Drawing Sheets

U.S. PATENT DOCUMENTS

| | | | |
|---|---|---|---|
| 3,873,432 | 3/1975 | Israel et al. | 204/180 G |
| 3,969,218 | 7/1976 | Scott | 204/299 R |
| 4,111,785 | 9/1978 | Roskam | 204/299 R |
| 4,138,551 | 2/1979 | Steiger et al. | 542/435 |
| 4,166,105 | 8/1979 | Hirschfeld | 424/8 |
| 4,256,834 | 3/1981 | Zuk et al. | 435/7 |
| 4,284,491 | 8/1981 | Vesterberg | 204/299 R |
| 4,337,063 | 6/1982 | Mihara et al. | 23/230 B |
| 4,351,709 | 9/1982 | Goetz | 204/180 |
| 4,375,401 | 3/1983 | Catsimpoolas | 204/301 |
| 4,404,289 | 9/1983 | Masuda et al. | 436/538 |
| 4,405,711 | 9/1983 | Masuda et al. | 435/4 |
| 4,414,325 | 11/1983 | Masuda et al. | 435/7 |
| 4,707,235 | 11/1987 | Englert et al. | 204/182.8 |
| 4,711,955 | 12/1987 | Ward et al. | 536/29 |
| 4,804,748 | 2/1989 | Seela | 536/28 |
| 4,810,348 | 3/1989 | Sarrine et al. | 204/299 R |
| 4,811,218 | 3/1989 | Hunkapiller et al. | 364/413.01 |
| 4,830,786 | 5/1989 | Pease et al. | 260/396 |
| 4,833,332 | 5/1989 | Robertson, Jr. et al. | 250/458.1 |
| 4,855,225 | 8/1989 | Fung et al. | 435/6 |
| 4,910,300 | 3/1990 | Urdea et al. | 536/287 |
| 4,948,882 | 8/1990 | Ruth | 536/27 |
| 4,981,977 | 1/1991 | Southwick et al. | 548/455 |
| 5,039,818 | 8/1991 | Pease et al. | 548/409 |
| 5,047,519 | 9/1991 | Hobbs, Jr. et al. | 536/23 |
| 5,091,519 | 2/1992 | Cruickshank | 536/29 |
| 5,106,990 | 4/1992 | Ohno et al. | 548/427 |
| 5,151,507 | 9/1992 | Hobbs, Jr. et al. | 536/23 |
| 5,171,534 | 12/1992 | Smith et al. | 422/82.05 |
| 5,187,085 | 2/1993 | Lee | 435/91 |
| 5,188,934 | 2/1993 | Menchen et al. | 435/6 |
| 5,241,060 | 8/1993 | Engelhardt et al. | 536/27 |
| 5,242,796 | 9/1993 | Prober et al. | 435/6 |
| 5,268,486 | 12/1993 | Waggoner et al. | 548/427 |
| 5,276,143 | 1/1994 | Sabesan et al. | 536/26.23 |
| 5,306,618 | 4/1994 | Prober et al. | 435/6 |
| 5,310,922 | 5/1994 | Pease et al. | 548/156 |
| 5,328,824 | 7/1994 | Ward et al. | 435/6 |
| 5,329,019 | 7/1994 | Pease et al. | 548/455 |
| 5,332,666 * | 7/1994 | Prober et al. | 435/91.5 |
| 5,366,860 | 11/1994 | Bergot et al. | 435/6 |

FOREIGN PATENT DOCUMENTS

| | | |
|---|---|---|
| 0 533 302 A1 | 3/1993 | (EP) . |
| 0 670 374 A1 | 2/1995 | (EP) . |
| 1529202 | 10/1978 | (GB) . |
| 1-239548 | 9/1989 | (JP) . |
| WO 83/02277 | 7/1983 | (WO) . |
| WO 93/16094 | 11/1993 | (WO) . |
| WO 94/06810 | 3/1994 | (WO) . |
| WO 95/04747 | 2/1995 | (WO) . |
| WO 95/07361 | 3/1995 | (WO) . |
| WO 96/00902 | 1/1996 | (WO) . |

OTHER PUBLICATIONS

Kunkel et al. "Fidelity of DNA Polymerase Used in Polymerase Chain Reactions" Current Communications in Molecular Biology, cold Spring Harbor Laboratory Press, pp. 5–10, 1989.*

Richardson et al. "Biotin and fluorescent labeling of RNA using T4 RNA ligase" Nucleic Acids Research, vol. 11, pp. 6167–6184, 1983.*

"A universal nucleoside for use at ambiguous sites in DNA primers"; R. Nichols, P.C. Andrews, P. Zhang & D. E,. Berstrom; *Nature*; vol. 369, Jun. 9, 1994, pp. 492–493.

"5–Nitroindole as an universal base analogue"; D. Loakes & D.M. Brown; *Nucleic Acids Research*; vol. 22, No. 20; pp. 4039–4043.

Synthesis, Structure, and Deoxyribonucleic Acid Sequencing with a Universal Nucleoside: 1–(2'–Deoxy–BD–ribofuranosyl)–3–nitropyrrole; Donald E. Bergstrom, Peiming Zhang, Pascal H. Toma, Philip C. Andrews, and Ruthann Nichols; *American Chemical Society*, vol. 117, No. 4, 1995; pp. 1201–1209.

"Aromatic Nonpolar Nucleosides as Hydrophobic Isosteres of Pyrimidine and Purine Nucleosides"; Barbara A. Schweitzer and Eric T. Kool; J. Org. Chem., 1994, vol. 59, No. 24; pp. 7238–7242.

"New Virtual Nucleotide VN$^{TM}$) Phosphoramidite and CPG Labeling Reagents"; *CLONTECHniques* Oct. 1994, pp. 12–13.

"Universal Nucleosides"; The Glen Report; vol. 7, No. 1; Sep. 1994.

"Spectral Characterization and Evaluation of Modified Near–Infrared Laser Dyes for DNA Sequencing" D. Shealy, R. Lohrmann, J. Ruth, N. Narayanan, S. Sutter, G. Casay, L. Evans, G. Patonay; *Applied Spectroscopy* vol. 49, No. 12, 1995; pp. 1815–1820.

"Steady–State and Picosecond Laser Fluorescence Studies of Nonradiative Pathways in Tricarbocyanine Dyes: Implications to the Design of Near–IR Fluorochromes with High Fluorescence Efficiencies"; S. Soper and Q. Mattingly; *American Chemical Society* 1994, pp. 3744–3752.

"Semiconductor Laser Fluorimetry in the Near–Infrared Region" by T. Imasaka, A Yoshitake and N. Ishibashi; *American Chemical Society*, 1984, pp. 1077–1079.

"Phase Fluorometry Using a Continuously Modulated Laser Diode" by R. Thompson, J. Frisoli and J. Lakowicz; *American Chemical Society* 1992; pp. 2075–2078.

"Solid–State Diode Laser–Induced Fluorescence Detection in High–Performance Liquid Chromatography" by S. Rahavendran and H. Karnes; *Pharmaceutical Research* vol. 10, No. 3, 1993, pp. 328–334.

"Near–Infrared Fluorogenic Labels: New Approach to an Old Problem" by G. Patonay and M. Antoine; *Analytical Chemistry*, vol. 63, No. 6, Mar. 15, 1991; pp. 321A–327A.

"Semiconductor laser–induced fluorescence detection in capillary electrophoresis using a cyanine dye" by F. Chen, A. Tusak, S. Pentoney, K. Konrad, C. Lew, E. Koh and J. Sternberg; *Journal of Chromatography* A, 652 (1993); pp. 355–360.

"Construction of a short–wave near infrared spectrofluorometer with diode laser source and charge–coupled device (CCD) detection" by J. Silzel and R. Obremski; SPIE vol. 1885 *Advances in Fluorescence Sensing Technology* 1993; pp. 439–447.

"A versatile infrared laser scanner/electrophoresis apparatus" by L. Middendorf, J. Bruce, R. Bruce, R. Eckles, S. Roemer, and G. Sloniker; SPIE vol. 1885 *Advances in Fluorescence Sensing Technology* (1993) pp. 423–434.

"Continuous, on–line DNA sequencing using a versatile infrared laser scanner/electrophoresis apparatus" by L. Middendorf, J. Bruce, R. Bruce, R. Eckles, D. Grone, S. Roemer, G. Sloniker, D. Steffens, S. Sutter, J. Brumbaugh, G. Patonay; *Electrophoresis* 1992, 13, pp. 487–494.

"Cyanine Dye Labeling Reagents Containing Isothiocyanate Groups" by R. Mujumdar, L. Ernst, S. Mujumdar and A. Waggoner; *Cytometry* 10:11–19 (1989).

"Cyanine Dye Labeling Reagents: Sulfoindocyanine Succinimidyl Esters" by R. Mujumdar, L. Ernst, S. Mujumdar, C. Lewis and A. Waggoner; *Bio–conjugate Chemistry* Mar./Apr. 1993, vol. 4, No. 2; pp. 105–111.

"Synthesis and duplex stability of oligonucleotides containing cytosine–thymine analogues" by P. Lin and D. Brown; *Nucleic Acids Research*; vol. 17, No. 24, 1989; pp. 10373–10383.

"Flexible Aglycone Residues in Duplex DNA" by P. Francois, D. Perilleux, Y. Kempener and E. Sonveaux; *Tetrahedron Letters* vol. 31, No. 44, pp. 6347–6350, 1990.

"Synthesis and duplex stability of oligonucleotides containing adenine–guanine analogues" by D. Brown and P. Lin; *Carbohydrate Research*; 216, 1991; pp. 129–139.

"Synthesis and biophysical studies of short oligodeoxynucleotides with novel modifications: a possible approach to the problem of mixed base oligodeozynucleotide synthesis" by T. Millican, G. Mock, M. Chauncey, T. Patel, M. Eaton, J. Gunning, S. Cutbush, S. Neidle and J. Mann; *Nucleic Acids Research* vol. 12, No. 19, 1984; pp. 7435–7453.

"An Alternative to the Mixed Probe Method in DNA Hybridization: Synthetic "lure" Nucleotide for the Ambiguous Position of Codons" by T. Fukuda, T. Kikuchi and R. Marumoto; pp. 1571–1579.

"Synthesis and properties of oligonucleotides containing 2'–deoxynebularine and 2'–deoxyxanthosine" dby R. Eritja, D. Howowitz, P. Walker, J. Ziehler–Martin, M. Boosalis, M. Goodman, K. Itakura and B. Kaplan; *Nucleic Acids Research* vol. 14, No. 20, 1986; pp. 8135–8153.

"Synthesis and hybridiztion of dodecadeoxyribonucleotides containing a fluorescent pyridopyrimidine deoxynucleoside" by H. Inoue, A. Imura and E. Ohtsuka; *Nucleic Acids Research*; vol. 13, No. 19, 1985; pp. 7119–7128.

"Stable Heptamethine Pyrylium Dyes That Absorb in the Infrared", G.A. Reynolds and K. H. Drexhage; *J. Org. Chem.* vol. 42, No. 5, 1977; pp. 885–888.

"Polymethine Dyes With Hydrocarbon Bridges. Enamino Ketones in the Chemistry of Cyanine Dyes", Y. L. Slominskii, I. D. Radchenko, S. V. Popov and A. I. Tolmachev; *Zhurnal Organicheskoi Knimii*, vol. 19, 1983, pp. 2134–2142 (Russian version) & pp. 1854–1860 (English translation).

"Synthesis of Meso–Substituted Tricarbocyanine Dyes With an Ortho–Phenylene Bridge in the Chromophore", G. M. Sosnovskii, A. P. Lugovskii and I. G. Tishchenko; *Zhurnal Organicheskoi Khimii*, vol. 19, 1983, pp. 2143–2146 (Russian version) and pp. 1861–1863 (English translation).

"Facile Derivatizations of Heptamethine Cyanine Dyes", L. Strekowski, M. Lipowska and G. Patonay; *Synth. Comm.*, vol. 22; 1992, pp. 2593–2598.

"Substitution Reactions of a Nucleofugal Group in Heptamethine Cyanine Dyes. Synthesis of an Isothiocyanato Derivative for Labeling of Proteins with a Near–Infrared Chromophore", L Strekowski, M. Lipowska and G. Patonay; *J. Org. Chem.* vol. 57, 1992, pp. 4578–4580.

"Comparison of Covalent and Noncovalent Labeling with Near–Infrared Dyes for the High–Performance Liquid Chromatographic Determination of Human Serum Albumin" R. J. Williams, M. Lipowska, G. Patonay, and L. Strekowski; *Anal. Chem.*, vol. 65, 1993, pp. 601–605.

"New Near–Infrared Cyanine Dyes for Labeling of Proteins" M. Lipowska, G. Patonay and L. Strekowski; *Synth. Comm.* vol. 23, 1994, pp. 3087–3094.

"Synthesis, Chromatographic Separation, and Characterization of Near–Infrared DNA Oligomers for Use in DNA Sequencing"; D. Shealy, M. Lipowska, J. Lipowski, N. Narayanan, S. Sutter, L. Strekowski and G. Patonay; *Anal. Chem.* vol. 67, 1995, pp. 247–251.

"A New Method for the Synthesis of Heptamethine Cyanine Dyes: Synthesis for New Near–Infrared Fluorescent Labels", N. Narayanan and G. Patonay; *J. Org. Chem.*, vol. 60, 1995, pp. 2391–2395.

"New Near Infrared Dyes for Applications in Bioanalytical Methods", N. Narayanan, G. Little, R. Raghavachari and G. Patonay; *Proc. Soc. Photo. Inst. Engr.*; 2388, 1995, pp. 6–14.

"Spectroscopic Studies of Near–Infrared Fluorophores and Their Evaluation as Fluorogenic Labels for Use in DNA Sequencing", Dana B. Shealy; Dissertation; 1994.

Salama, G., et al., Sulfhydryl Reagent Dyes Trigger the Rapid Release of $Ca^{2+}$ from Sarcoplasmic Retriculum Vesicles (SR); Biophysical Journal, vol. 47, 456A (1985).

A. S. Waggoner, et al. The Kinetics of Conformational Changes in a Region of the Rhodopsin Molecule Away from the Retinylidene Binding Site; *Biophysical Journal*, vol. 33, 292a (1981).

Jacobson, et al. Interational Workshop on the Application of Fluorescence Photobleaching Techniques to Problems in Cell Biology; Federation Proceedings, vol. 42, 72–79 (1973).

R. M. McKinney, et al. An Approach to Quantitation in Rhodamine Isothiocyanate Labeling; *Annals N.Y. Acad of Sciences*, vol. 254, pp. 55–65 (1975).

K. A. Muirhead, et al. Flow Cytometry: Present and Future; *Review, Biotechnology*, vol. 3 (Apr. 1985).

J. S. Ploem, General Introduction; Fifth International Conference on Immunofluorescence and Related Staining Technique, *Annals of the N.Y. Academy of Sciences*, vol. 254, pp. 1–20 (1975).

F. Hamer; Cyanine Dyes and Related Compounds; *Interscience Publishers*, pp. 86–350, 398–399, 460–463, 482–495 and 511–513, (1964).

M. R. Loken, et al. Lymphoid Cell Analysis and Sorting; *Flow Cytometry and Sorting*, pp. 505, 522–523, (1979).

R. P. Haugland; Covalent Fluorescent Probes; *Excited States of Biopolymers*, Plenum Press; pp. 29–58 (1982).

* cited by examiner

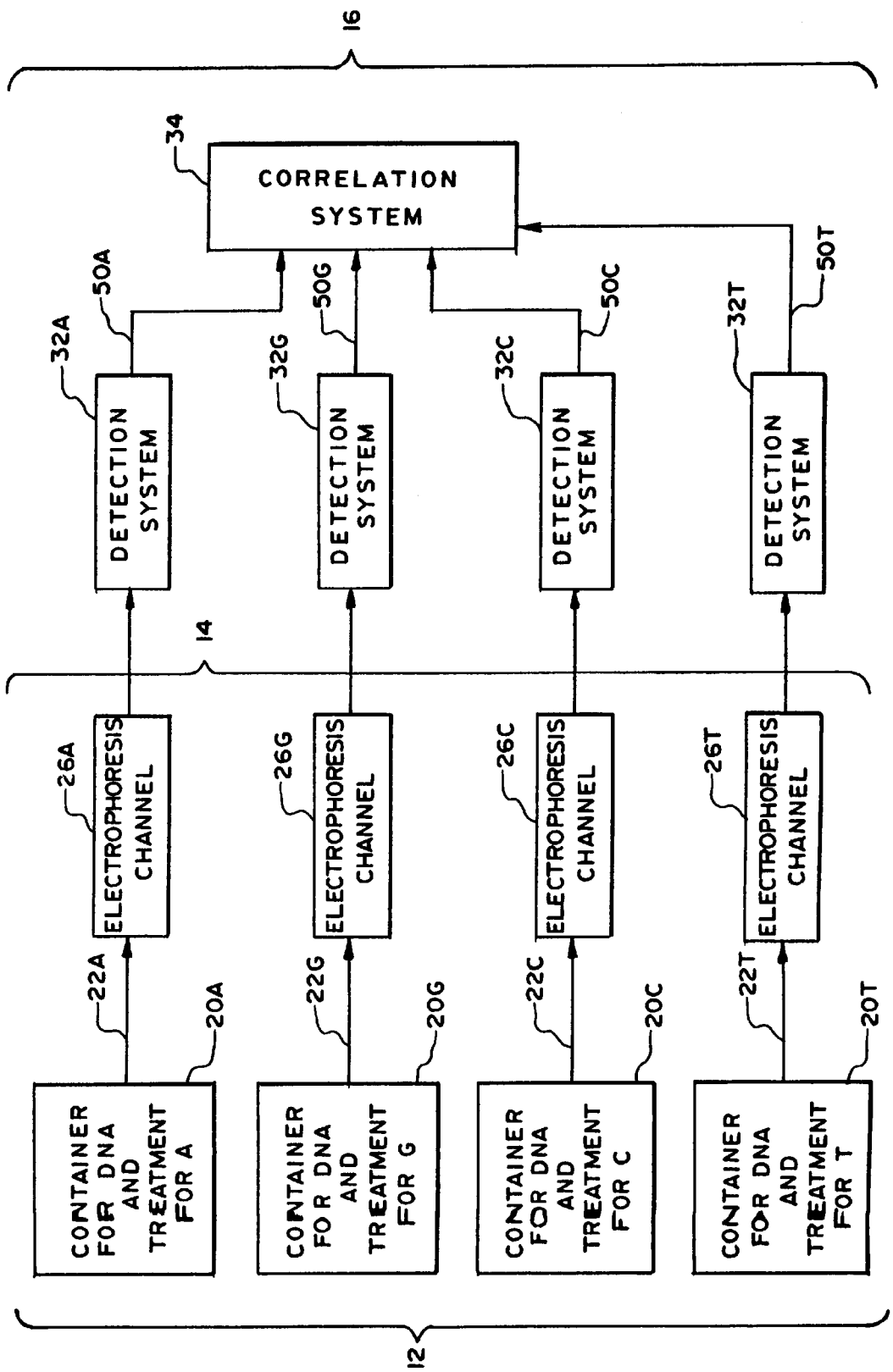

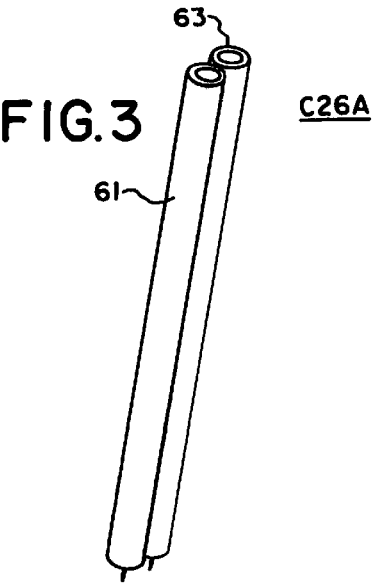
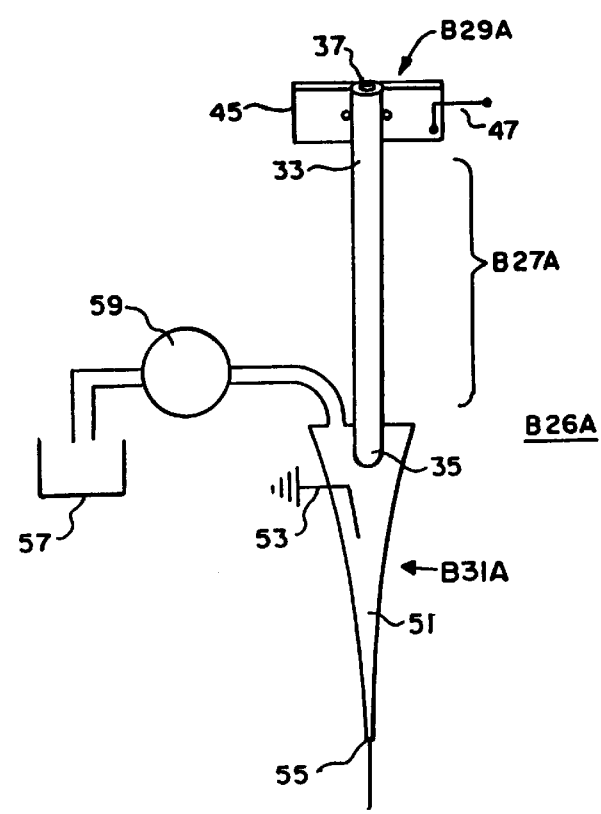
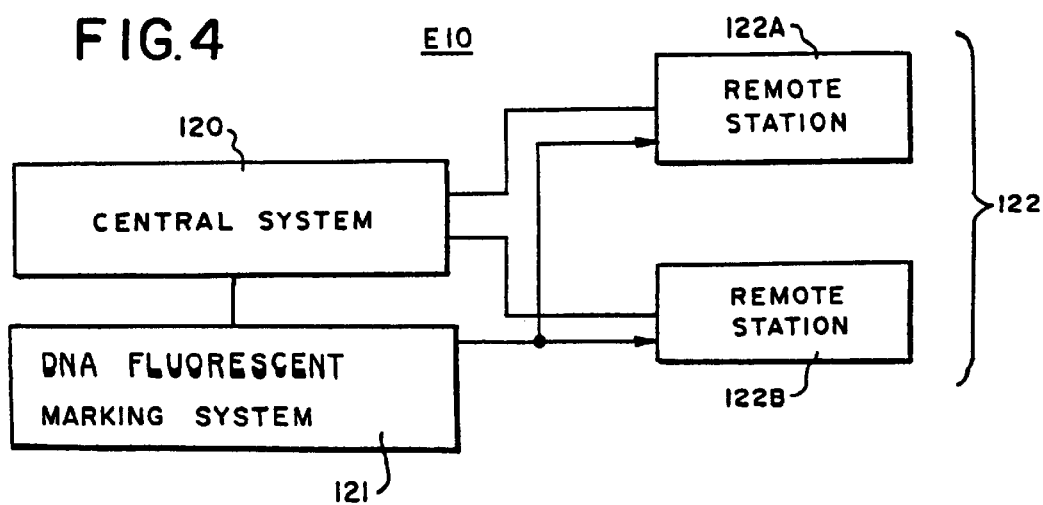

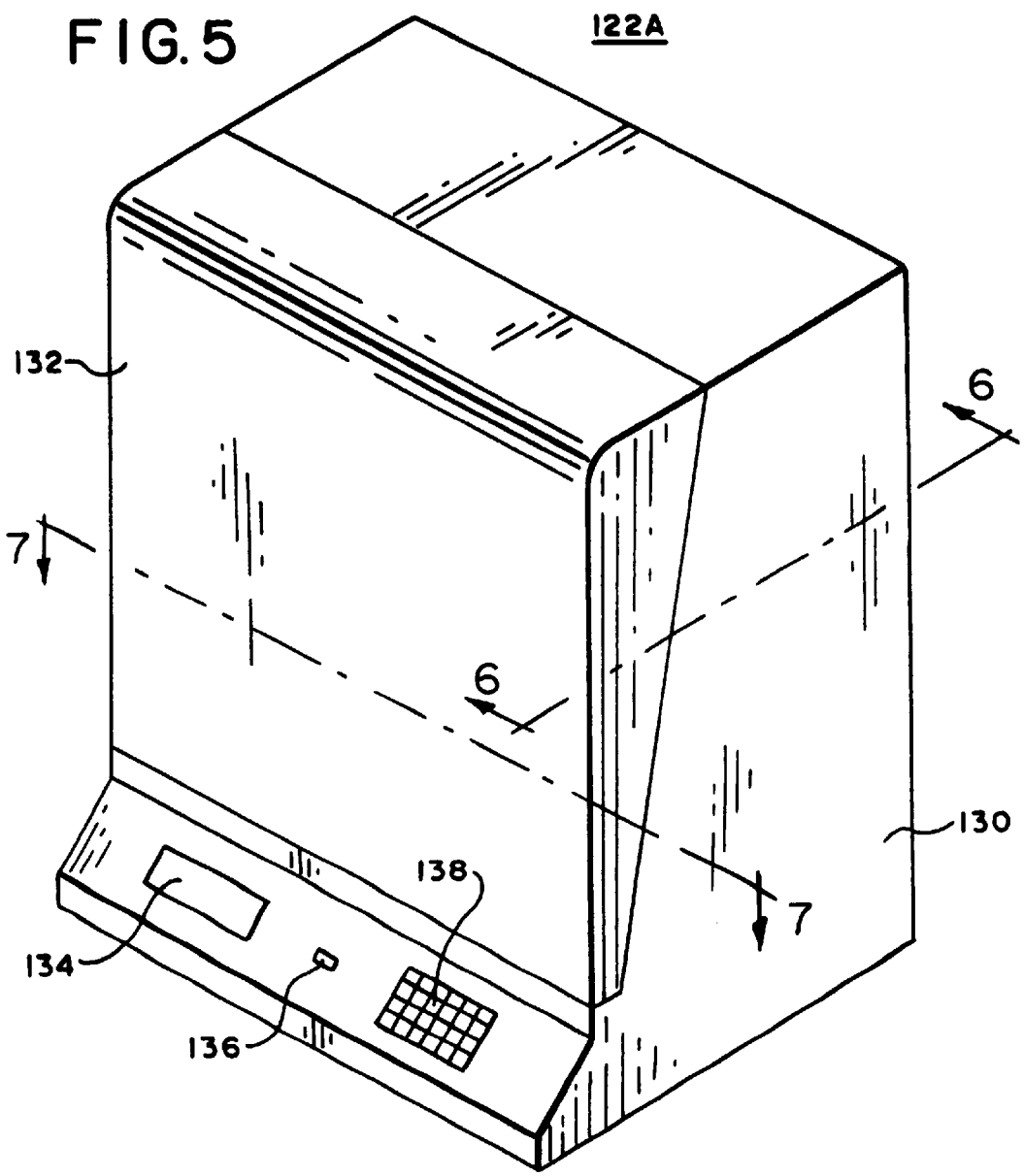

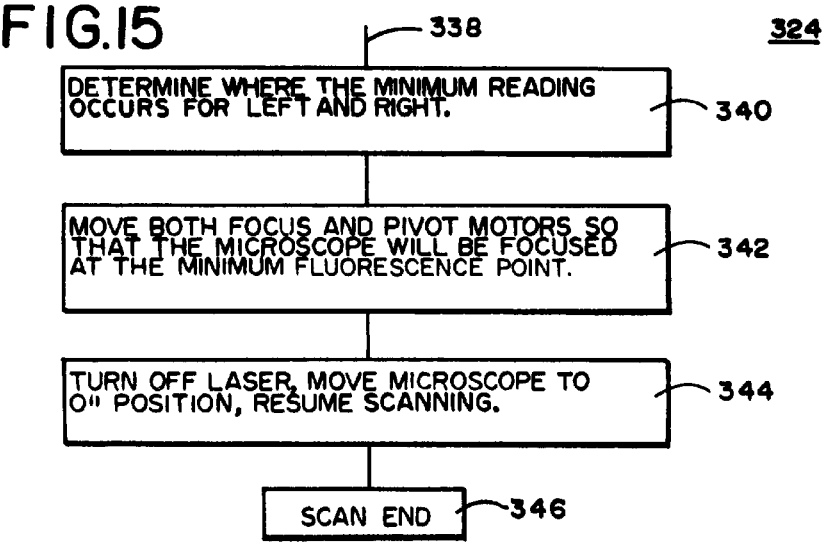
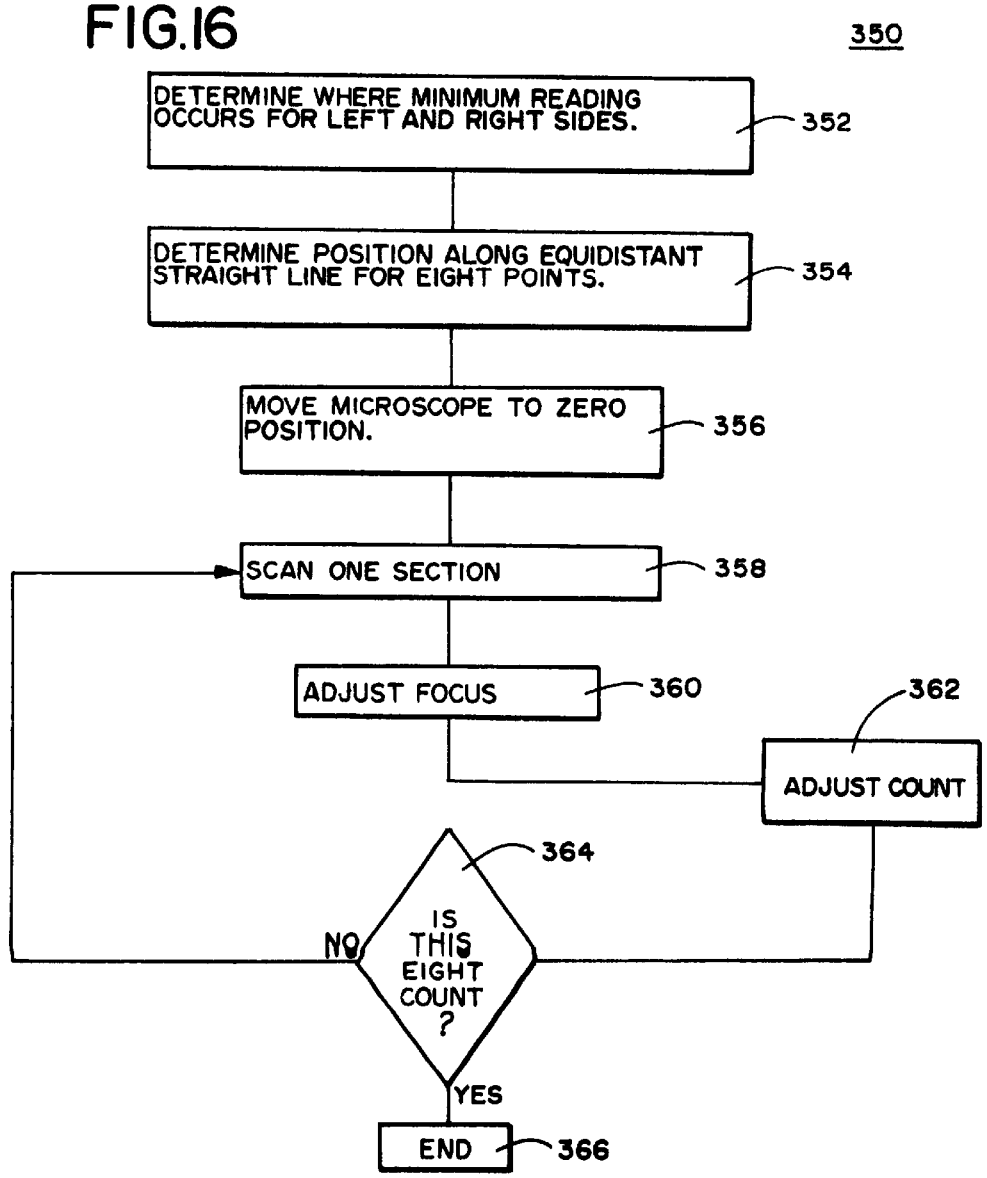

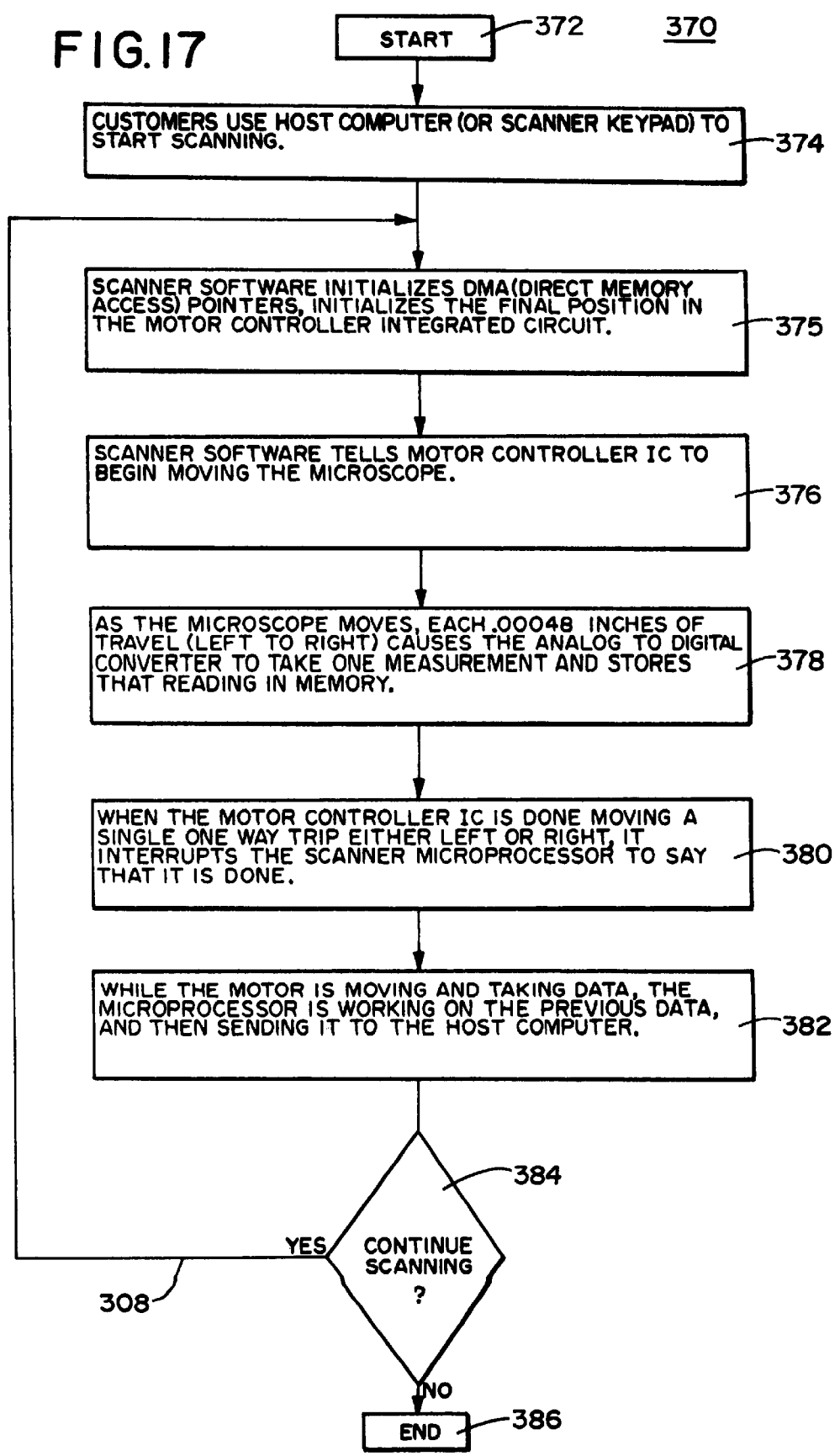

DNA SEQUENCING AND DNA TERMINATORS

REFERENCE TO RELATED APPLICATIONS

This application is a continuation-in-part of U.S. patent application Ser. No. 08/275,232, filed Jul. 14, 1994, abandoned, which is a divisional application of U.S. application Ser. No. 07/950,734, filed Sep. 24, 1989, now U.S. Pat. No. 5,346,603, which is a file wrapper continuation of Ser. No. 07/799,712 filed Nov. 6, 1991 (abandoned) which is a file wrapper continuation of Ser. No. 07/632,605, filed Dec 24, 1990, (abandoned), which is a file wrapper continuation of Ser. No. 07/078,279, filed Jul. 27, 1987 (abandoned), which is a divisional of U.S. application Ser. No. 06/594,676, filed Mar. 29, 1984, in the names of Lyle Richard Middendorf and John Brumbaugh now U.S. Pat. No. 4,729,947, and assigned to the same assignee as this application and is a continuation-in-part of U.S. patent application Ser. No. 08/288,461 filed Aug. 10, 1994 (now U.S. Pat. No. 5,534,125), which is a division of U.S. patent application Ser. No. 08/018,806, filed Feb. 17, 1993 now U.S. Pat. No. 5,360,523, which is a division of U.S. application Ser. No. 07/763,230, filed Sep. 20, 1991, (now U.S. Pat. No. 5,230,781) and of U.S. application Ser. No. 07/570,503 filed Aug. 21, 1990, (now U.S. Pat. No. 5,207,880) which are continuations in part of Ser. No. 07/078,279 filed Jul. 27, 1987, which is a division of U.S. application Ser. No. 06/594,676 for DNA SEQUENCING filed by Middendorf et al., on Mar. 29, 1984, and assigned to the same assignee as this application, now U.S. Pat. No. 4,729,947, and a continuation-in-part of U.S. application Ser. No.08/204,627, filed Mar. 1, 1994, now U.S. Pat. No. 5,571,388 which is a continuation-in-part of U.S. application Ser. No. 07/860,140, filed Mar. 30, 1992, now U.S. Pat. No. 5,366,603 which is a division of U.S. application Ser. No. 07/763,230 filed Sep. 20, 1991, now U.S. Pat. No. 5,230,781, which is a continuation-in-part of U.S. application Ser. No. 07/570,503 filed Aug. 21, 1990, now U.S. Pat. No. 5,207,880, which is a continuation-in-part application of Ser. No. 07/078,279 filed Jul. 27, 1987, which is a division of U.S. application Ser. No. 06/594,676 for DNA SEQUENCING filed by Middendorf et al., on Mar. 29, 1984, and assigned to the same assignee as this application, now U.S. Pat. No. 4,729,947.

BACKGROUND OF THE INVENTION

This invention relates to DNA terminators for signaling the end of DNA strand synthesis which may be used to prepare DNA strands and for sequencing and to the marking and sequencing of DNA strands.

In one class of techniques for sequencing DNA, identical strands of DNA are marked. The strands are separated into four aliquots. The strands in a given aliquot are either individually cleaved at or synthesized to any base belonging to only one of the four base types, which are adenine, guanine, cytosine and thymine (hereinafter A, G, C and T). The adenine-, guanine-, cytosine- and thymine-terminated strands are then electrophoresed for separation. The different marked strands are detected and the terminating base identified for each. The rate of electrophoresis of the different terminated base strands indicates the DNA sequence.

In one class of technique for marking DNA strands, the strands are marked with a fluorescent dye. The strands are marked by: (1) hybridzing specially synthesized fluorescently marked oligonucleotide primer strands to template strands of DNA and then extending the primer strands with DNA polymerase to incorporate unmarked deoxy nucleotide triphosphates and an unmarked terminator such as a dideoxynucleotide triphosphate for the purpose of uniquely terminating strand synthesis; (2) hybridizing unmarked oligonucleotide primer strands to template strands and then extending the primer strands with DNA polymerase to incorporate marked deoxynucleotide triphosphates and an unmarked terminator such as a dideoxy nucleotide triphosphate for the purpose of uniquely terminating strand synthesis; or (3) hybridizing unmarked oligonucleotide primer strands with DNA polymerase to incorporate unmarked deoxynucleotide triphosphates and a marked terminator such as a dideoxy nucleotide triphosphate for the purpose of uniquely terminating strand synthesis.

In a prior art technique of this class, the marked strands are of four types, each corresponding to the appropriate one of adenine-, guanine-, cytosine-, and thymine-terminated strands. Moreover, in prior art sequencing techniques of this class, the fluorescent dyes used as markers have their maximum emission spectra in the visible range with wavelengths shorter than 650 nm, the DNA is subject to irradiation in this visible spectra, and visible spectra detectors and light sources are used. Generally photomultipliers tubes are used for detection and gas lasers such as Argon-ion or Helium—Neon lasers are used as light sources.

Cyanine dyes are known to absorb far red (600–700 nm) and near infrared (700–1200 nm) light and techniques for the synthesis of derivatives of the cyanine dyes are known. The use of cyanine dyes as markers for DNA sequencing has been successfully achieved as described by Middendorf, L. R., et al., "Electrophoresis Journal" 13, 487–494 (1992).

An additional disadvantage of the prior art techniques for DNA sequencing is the need to have four different terminators, regardless of whether or not they are marked, for the purpose of providing a unique termination of strand synthesis.

In a prior art sequencing technique, the DNA strands are marked with a radioactive marker, and after being separated by electrophoresis, film is exposed to the gel and developed to indicate the sequence of the bands. The range of lengths and resolution of this type of static detection is limited by the size of the apparatus.

The prior art techniques for DNA sequencing have several disadvantages such as: (1) because the dyes have their emission spectra in that visible region of the light spectrum having a wavelength shorter than 650 nm, the lasers used to excite the fluorescent markers, and under some circumstances, the detectors for the light tend to be expensive; (2) the signal information is relatively noisy due to the background fluorescence interference by biomolecules and glass; (3) they are relatively slow; (4) they are at least partly manual; (5) they are limited to relatively short strands of DNA; (6) they do not have high sensitivity; and (7) they required complex protocols involving multiple types of synthesis terminators.

SUMMARY OF THE INVENTION

Accordingly, it is an object of the invention to provide a novel technique for DNA termination.

It is a further object of the invention to provide a novel technique for marking DNA strands.

It is a still further object of the invention to provide a novel technique for DNA sequencing.

It is a still further object of the invention to provide a novel technique for terminating DNA strand synthesis.

It is a still further object of the invention to provide a novel universal terminator for DNA sequencing.

It is a still further object of the invention to provide novel apparatuses and methods for sequencing relatively large fragments of DNA.

It is a still further object of the invention to provide novel apparatuses and methods for sequencing DNA fragments of 100 bases or more.

It is a still further object of the invention to provide a technique for continuous sequencing of DNA.

It is a still further object of the invention to continuously sequence DNA without the spatial limitations of range of lengths and resolution.

It is a still further object of the invention to provide a novel technique for continuously sequencing DNA using fluorescent detection.

It is a still further object of the invention to provide a novel technique for continuously sequencing DNA marked with fluorescence which more clearly distinguishes marked DNA fragments from background fluorescence.

It is a still further object of the invention to provide a novel technique for scanning fluorescent material.

It is a further object of the invention to provide novel equipment and methods for the sequencing of far red and/or infrared but especially far red (600–700 nm) and/or near infrared (700–3000 nm) fluorescence labeled DNA and the detection of the DNA after irradiation by light from laser diodes.

It is a still further object of the invention to provide a novel technique for DNA sequencing using a novel fluorescent marker attached to the DNA.

It is a still further object of the invention to provide a novel fluorescent marker, method of synthesizing the marker and of attaching it to DNA.

It is a further object of the invention to provide a novel method, marker and equipment that permits the detection of marked molecules, including DNA, using diode light sources such as laser diodes or light emitting diodes and semiconductor detectors such as photodiodes or charge-coupled devices (CCD's).

In accordance with the above and further objects of the invention, strands of DNA are prepared and continuously electrophoresed and identified. For this purpose, the strands are fluorescently marked. The light emitted while irradiating the strands near the terminal end of the electrophoresis channel is detected and correlated. The electrophoresis conditions are selected so that strands being electrophoresed near the terminal end of the electrophoresis channel are fully resolved prior to the resolution of longer strands that have not yet reached the terminal end of the electrophoresis channel, and so on, in a continuous process over a period of time.

The gel size, electric field and DNA mobilities are such that the first bands to be moved completely through the gel are fully resolved while the last bands are yet unresolved in a continuous process controlled to cause at least ten percent of the bands to be resolved and electrophoresed through the gel while the less mobile bands are yet unresolved near the entrance end of the gel. These less mobile bands become resolved little by little over time in a continuous fashion without interruption of the movement of these bands through the gel.

In one embodiment for labeling strands, a substrate that terminates synthesis is labeled with a marker. In another embodiment, the strand is labeled either by a labeled primer that provides the initial portion of the strand or by a labeled deoxy nucleotide triphosphate that allows labeling of the strand during elongation. In any of these embodiments, it is preferable for the substrate that terminates synthesis to have a heterocycle other than naturally occuring DNA heterocycles such as adenine, cytosine, guanine and thymine. Alternatively, the substrate may have a modified base or sugar or be missing either the base or sugar (or both structures).

In terminating the strand synthesis, a universal terminator substrate (which may or may not be marked) is used. In this specification, the word "universal" as applied to terminator substrates means a terminator substrate that can be incorporated by DNA polymerase at any A, G, T or C position. In this specification the word "terminator" means a substrate that once incorporated by the DNA polymerase into a growing DNA strand, it will cause termination of the DNA polymerase activity on that strand.

One step in terminating strand synthesis is to design a universal terminator that has a lower incorporation efficiency than a normal "A", "C", "G", "T" deoxynucleotide. In this specification "a lower incorporation efficiency" means that the DNA polymerase reactivity for normal deoxynucleotides is at least five times higher than for the universal terminator substrate. Incorporation efficiency of a substrate is related to the relative reactivity of a DNA polymerase with respect to normal deoxynucleotide triphosphates as compared to the reactivity of a polymerase to the substrate. For example the reactivity of Taq polymerase is about 10,000 times higher for deoxynucleotide triphosphates than for dideoxy nucleotide triphosphates. For Sequenase polymerase (Sequenase is a trademark of U.S. Biochemical Corporation) the reactivity is between one and five times higher for deoxynucleotide triphosphates than for dideoxy nucleotide triphosphates.

In terminating strand synthesis, the hybridized primer-template is split into four aliquots. In the "A" vial is added DNA polymerase and normal amounts of "C", "G", and "T" deoxynucleotides, along with a reduced amount of "A" deoxynucleotide and an amount of the universal terminator such that statistically the universal terminator has less than a one percent chance of being incorporated at sites where a "C", "G", or "T" deoxynucleotide should be incorporated and about a one percent chance of being incorporated at sites where an "A" deoxynucleotide should be incorporated. The amount of "A" deoxynucleotide and universal terminator added may be modified to give a different chance than one percent depending on the desired length of the terminated strand as well as accomodate universal terminator substrates that have equivalent incorporation efficiencies as normal deoxynucleotides. No "A", "C", "G" or "T" dideoxynucleotides are used. In one embodiment the primer is marked. In another embodiment one or more of the deoxynucleotides is marked. In still another embodiment the terminator is marked.

At each position of adding substrate, if a "C", "G", or "T" deoxynucleotide is to be added, it is preferentially added rather than the universal terminator (even though the universal terminator theoretically could be added at any "A", "C", "G" or "T" position) due to the much lower incorporation efficiency by the DNA polymerase for the universal terminator and/or a reduction in the amount of universal terminator present in the sequencing reaction. However, at each position where an "A" is to be added, the DNA polymerase may statistically incorporate either the "A" deoxynucleotide or the universal terminator since the "A" deoxynucleotide concentration is reduced. The result is a batch of differing length strands, each of which is terminated by the universal terminator at any one of the "A" positions.

Similar strategies are followed for the "C", "G", and "T" vials, except that the amount of "C", "G" and "T" deoxynucleotides are reduced for their respective vial. The same type of universal terminator is used in all four vials. In the preferred embodiment, the marked strands are electrophoresed in a continuous, on-line process and detected.

In one embodiment, the primers are far red or near infrared wavelength fluorescent labeled DNA and the detection of the DNA after irradiation by far red or near infrared light from a laser diode is accomplished using a novel label attached to the primer. In this embodiment only one type of labeled primer and only one type of universal terminator is required for the "A", "C", "G" and "T" reactions. An extention of this embodiment employs multiple types of labels differentiated by optical characteristics such as absorbance wavelength, emission wavelength, fluorescence lifetime, or a combination of such. Thus, multiple types of primer labeled strands can be optically differentiated even though all strands are terminated with the identical type of universal terminator.

In a second embodiment the primers are unlabeled and the universal terminator is marked, thus it is a universal labeled terminator. Again, only one type of unlabeled primer and only one type of universal labeled terminator is required for the "A", "C", "G" and "T" reactions. An extension of this embodiment employs multiple types of labels differentiated by characteristics such as absorbance wavelength, emission wavelength, fluorescence lifetime, or a combination of such. Thus, each set of "A", "C", "G" and "T" strands uses one unique universal labeled terminator. Sets are discriminated by the specific optical uniqueness of the universal labeled terminator used to create each set.

The strands of DNA are continuously electrophoresed and identified for DNA sequencing. To aid in identification, the strands are marked with fluorescent labels that emit light in the far red (600–700 nm) or near infrared (700–3000 nm) region. The strands are irradiated with light in the far red or near infrared region and the light emitted from the fluorescent labels is detected and used to obtain information about the DNA strands. In one embodiment, the strands are detected by irradiating with a far red or near infrared laser diode light source.

The detection apparatus includes a laser diode that emits light of a wavelength near or in the optimum absorbance spectrum of the marker. In the preferred embodiment, the light source is a laser diode that irradiates channels of DNA strands with far red or near infrared light having a wavelength that matches the absorbance region of the marker. The detector includes a light sensor which is preferably an avalanche photodiode sensitive to the far red or near infrared light emission of the marker. It may include a filtering system having a pass band suitable for passing selectively the optimum emission of the fluorescent marker to the light sensor.

The photodiode, photomultiplier or other light sensor selectively detects the fluorescence, using techniques which enhance the signal/noise ratio. One technique is to modulate the laser source by pulsing the electrical current driving the laser, with detection facilitated by a lock-in amplifier. The detection is made in a wavelength band including the high emission spectrum of the fluorescent marker.

The apparatus for such continuously sequencing of DNA includes one or more electrophoresis channels, each adapted to receive fluorescently labeled DNA strands, having at one end a universal terminator substituted for a base of a given type.

To provide marking, either a fluorescent marker is attached to the DNA fragments prior to their being electrophoresed, or probes are used to combine or hybridize with the DNA strands. In the latter case, the detection is accomplished by detecting a fluorescent marker that is chemically attached to the probe. In the preferred embodiment, the marker is a dye that fluoresces in the far red or near infrared region.

The electrophoresis may be provided in conventional gel slabs or in tube gels such as gel filled capillary tubes or buffer filled capillary tubes which avoid the need for gel and make the cleaning more convenient.

For the configuration using conventional gel slabs, one embodiment provides for a different input section for each of four channels that are for a corresponding one of the A, G, T and C strands. Other embodiments allow for less than four gel channels by judiciously combining one or more base types A, G, T, or C in a channel. The strands are detected during electrophoresis either in the gel by scanning back and forth across the gel at a fixed distance from the entrance end of the gel or by one or more fixed detectors located at a fixed distance from the entrance end of the gel or after leaving the gel. The strands are detected in a manner that indicates their mobility in the gel to indicate the sequence of the A, G, C and T strands of different lengths.

The detection apparatus includes a light source, such as a laser diode or light-emitting diode or other suitable source that emits light in the optimum absorbance spectrum of the marker. The light may be split by the use of fiber optics or other conventional optical components so there is a light source for each channel.

In the preferred embodiment, the light source is a laser diode that irradiates the channels with far red or near infrared light having a wavelength that matches the absorbance region of the marker. The detector includes a light sensor which is preferably an avalanche photodiode sensitive to the far red or near infrared light emission of the marker. It may include a filtering system having a pass band suitable for passing selectively the optimum emission of the fluorescent marker to the light sensor.

Correlation of the channel in which the fluorescent light is detected and the time of detection of the fluorescent light indicates: (1) if the type of universal termination is A, G, C or T or a combination thereof for those embodiments which have more than one base type in a channel; and (2) the time sequence of separation of each strand in each channel of the electrophoresis gel. This information, in turn, indicates the overall sequence of strands.

To use the apparatus to sequence DNA strands, identical DNA strands are normally formed of a length greater than 100 bases. In one embodiment, the strands are marked by a suitable marker at one end. The strands are divided into four aliquots and the strands within each aliquot are synthesized to any base belonging to a specific base type. These four aliquots are then electrophoresed through one or more identical channels to separate strands so that the shorter strands are resolved towards the end of the gel prior to resolution of the longer strands, which may be near the entrance end of the gel at the time the shorter strands are being resolved. This occurs in a continuous process so a substantial number of different length strands may be resolved in a relatively short gel. This methodology takes advantage of time-resolved bands, as opposed to the limitations of spatial-resolved bands.

The gel size, electric field and DNA mobilities are such that the more mobile bands are fully resolved while the less mobile bands are yet unresolved in a continuous process such that at least ten percent of the bands have been resolved by electrophoresis in the gel while the less mobile bands which are near the entrance end of the gel are not fully resolved. These less mobile bands become resolved little by little over time in a continuous fashion without interruption of the movement of these bands through the gel. The markers are detected by transmitting far red or near infrared light to fluorescently marked DNA strands.

To obtain maximum information in those embodiments in which a gel slab is scanned, a microscope and laser are moved together on a platform with respect to the gel. To ensure parallelism between the microscope/laser assembly and the slab gel as well as optimal focusing of the assembly onto the slab gel, in one embodiment, the sensor determines the point in the glass-gel-glass sandwich having minimal fluorescence and focuses on it. This minimal fluorescence is due to the reduced fluorescence of the gel as compared to the glass. The microscope is continually moved and refocused as scanning takes place to maintain the optimum focus.

In another scanning embodiment, the microscope determines the optimal focus position at one location on the glass-gel-glass sandwich and then is moved to another location on the glass-gel-glass sandwich where an optimal focus position is determined for that location. The scanning mechanism is then pivoted so that the scanning mechanism is parallel to a line connecting the two optimal focus positions previously determined. This insures that the gel slab is in the focal plane of the microscope/laser assembly. The intensity signal received from the scanning microscope/laser assembly which indicates the presence or absence of DNA strands is directly transmitted to the intensity input of the computer monitor so that the display varies in brightness rather than providing an amplitude trace.

For purposes of focusing, either by pivoting the scanning mechanism or by adjusting the microscope at different points during a scan to follow an established line, the microscope/laser assembly and the plane of the glass-gel-glass sandwich move orthogonally with respect to each other at one end of the scan in order to locate the position of lowest fluorescence, which is a location in the gel slab between the two glass plates. Then the microscope/laser assembly moves to the other end of its scan and performs the same function. These two focusing movements are utilized to move the scan mechanism in one embodiment and to program the movement of the microscope focus in another embodiment so that the microscope in the one embodiment moves continuously along a single line and the scan mechanism has been prepositioned such that that line is parallel to the gel slab, and in the other embodiment, the focus is changed at six points to accommodate a non-parallel alignment between the scan mechanism and the gel.

From the above summary, it can be understood that the sequencing techniques of this invention have several advantages, such as: (1) they take advantage of resolution over time, as opposed to space; (2) they are continuous; (3) they are automatic; (4) they are capable of sequencing or identifying markers in relatively long strands including strands of more than 100 bases; (5) they are relatively economical and easy to use; (6) they permit efficient focusing of a light sensor onto the DNA bands; (7) they provide an easy to observe display; (8) because the dyes have their emission spectra in the far red or near infrared light spectrum, small inexpensive far red or near infrared laser diodes may be used; (9) the signal information is characterized by relatively low noise; and (10) they provide a simple protocol using universal termination of strands elongated by DNA polymerase.

SUMMARY OF THE DRAWINGS

The above noted and other features of the invention will be better understood from the following detailed description when considered with reference to the accompanying drawings in which:

FIG. 1 is a block diagram of an embodiment of the invention;

FIG. 2 is one embodiment of a portion of the DNA sequencing apparatus of FIG. 1;

FIG. 3 is another embodiment of a portion of the DNA sequencing apparatus of FIG. 1;

FIG. 4 is a block diagram of an embodiment of the invention;

FIG. 5 is a perspective view of a portion of the embodiment of FIG. 4;

FIG. 15 is a schematic diagram of another portion of the program of FIG. 13;

FIG. 16 is a block diagram of another embodiment of the program of FIG. 15;

FIG. 17 is a block diagram of a control portion for the embodiments of FIGS. 1–16;

DETAILED DESCRIPTION

Figure 6:
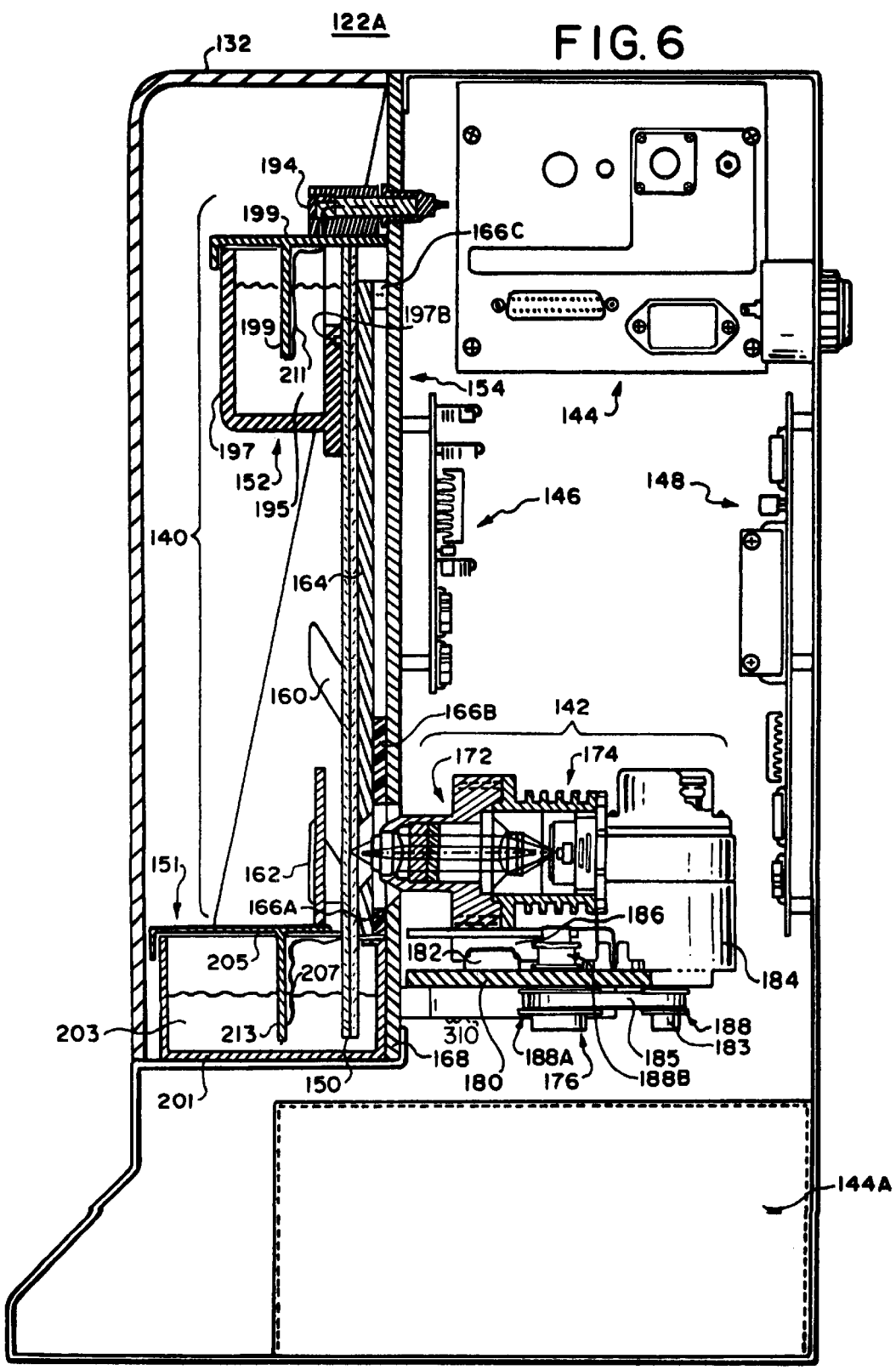
FIG. 6 is a sectional view taken through lines 6—6 of FIG. 5.

In FIG. 1, there is shown a simplified block diagram of a DNA sequencing system 10. In this embodiment, the DNA sequencing system 10 includes containers for treatment of the DNA in accordance with the method of Sanger described by F. Sanger, S. Nicklen and A. R. Coulson, "DNA Sequencing with Chain-Terminating Inhibiters," *Proceeding of the National Academy of Science, USA,* Vol. 74, No. 12, 5463–5467, 1977 indicated in the embodiment 10 of FIG. 1 at 20A, 20G, 20C and 20T shown as a group generally at 12.

In this method, DNA strands are used as templates to synthesize DNA with synthesis terminating at given base types A, G, C or T in a random manner to obtain a plurality of different molecular weight strands. The limited synthesis is obtained by using nucleotides which will terminate synthesis and is performed in separate containers, one of which has the special A nucleotide, another the special G nucleotide, another the special C nucleotide and another the special T nucleotide. These special nucleotides may be dideoxy nucleotides or marked nucleotides, both of which would terminate synthesis. So, each of the four batches will be terminated at a different one of the types of bases A, G, C and T randomly.

In one embodiment for labeling strands, a substrate that terminates synthesis is labeled with a marker. In another embodiment, the substrate that terminates synthesis is unlabeled but the strand is labeled either by a labeled primer that provides the initial part of the strand or by a labeled deoxy nucleotide triphosphate that allows labeling of the strand during elongation. In either embodiment, it is preferable for the substrate that terminates synthese to have a heterocycle other than naturally occuring DNA heterocycles such as adenine, cytosine, guanine or thymine. Additionally, the substrate may have a modified base or sugar (or both structures).

In the preferred embodiment for terminating the strand synthesis, a universal terminator substrate (which may or may not be marked) is designed to have a lower incorporation efficiency than a normal "A", "C", "G", "T" deoxynucleotide. In this specification "a lower incorporation efficiency" as applied to a universal terminator substrate means that the DNA polymerase reactivity for normal deoxynucleotides is at least five times higher than for the universal terminator substrate. In another embodiment, the incorporation efficiency of the universal terminator is nearly the same as for normal deoxynucleotides. In this embodiment, the amount of universal terminator used in a Sanger sequencing reaction is reduced.

Incorporation efficiency of a substrate is related to the relative reactivity of a DNA polymerase with respect to normal deoxynucleotide triphosphates as compared to the reactivity of a polymerase to the substrate. For example, the reactivity of Taq polymerase is about 10,000 times higher for deoxynucleotide triphosphates than for diodeoxynucleotide triphophates. For Sequenase polymerase (sequenase is a trademark of U.S. Biochemical Corporation) the reactivity is between one and five times higher for deoxynucleotide triphosphates than for dideoxynucleotide triphosphates. In this specification, the word "universal" as applied to terminator substrates means a terminator substrate that can be incorporated by DNA polymerase at any A, G, T or C position. In this specification, the word "terminator" means a substrate that once incorporated by the DNA polymerase into a growing DNA strand, it will cause termination of the DNA polymerase activity on that strand.

In terminating strand synthesis, the hybridized primer-template is split into four aliquots. In the "A" vial is added DNA polymerase and normal amounts of "C", "G", and "T" deoxynucleotides, along with a reduced amount of "A" deoxynucleotide and an amount of the universal terminator such that statiscally the universal terminator has less than a one percent chance of being incorporated at sites where a "C", "G", or "T" deoxynucleotide should be incorporated, and about a one percent chance of being incorporated at sites where an "A" deoxynucleotide should be incorporated.

The amount of "A" deoxynucleotide and universal terminator added may be modified to give a different chance than one percent depending on the desired length of the terminated strand as well as accomodate universal terminator substrates that have equivalent incorporation efficiencies as normal deoxynucleotides. No "C", "G" or "T" dideoxynucleotides are used. In the first embodiment, the universal terminator is marked. In the second embodiment, the universal terminator is unmarked, and the strand is marked either prior to elongation by DNA polymerase of a labeled primer oligonucleotide, or during elongation by the DNA polymerase through the incorporation of a marked "C", "G" or "T" deoxynucleotide.

At each position of adding substrate, if a "C", "G", or "T" deoxynucleotide is to be added, it is preferentially added rather than the universal terminator (even though the universal terminator theroretically could be added at any "A", "C", "G" or "T" position) due to the lower incorporation efficiency by the DNA polymerase for the universal terminator and/or a reduced amount of universal terminator present in the sequencing reaction. However, at each position where an "A" is to be added, the DNA polymerase may statistically incorporate either the "A" deoxynucleotide or the universal terminator since the "A" deoxynucleotide concentration is reduced. The result is a batch of differing length strands, each of which is terminated by the universal terminator at any one of the "A" positions.

Similar strategies are followed for the "C", "G", and "T" vials, except that the amount of "C", "G" and "T" deoxynucleotides are reduced for their respective vial. The same type of universal terminator is used in all four vials. The strands are loaded into four electrophoresis channels and continuous, on-line detection is used.

In the second embodiment, the Sanger sequencing protocol for a given DNA template uses labeled primers and also requires only one type of universal terminator dd*TP for all the four reactions: (where * indicates a universal base—usually a heterocyclic compound as a substitute for the adenine, cytosine, guanine or thymine base). (In the first embodiment the dd*TP is marked with dye label and the primer is not labeled). In these four reactions of the second embodiment: (1) the "A" reaction has the following components: a template, a labeled primer, a buffer, dCTP, dGTP, dTTP, an adjusted amount of dATP and dd*TP and a DNA polymerase enzyme; (2) the "C" reaction has the following components: a template, a labeled primer, a buffer, dATP, dGTP, dTTP, an adjusted amount of dCTP and dd*TP and a DNA polymerase enzyme; (3) the "G" reaction has the following components: a template, a labeled primer, a buffer, dATP, dCTP, dTTP, an adjusted proportional amount of dGTP and dd*TP and a DNA polymerase enzyme; and (4) the "T" reaction has the following components: a template, a labeled primer, a buffer, dATP, dCTP, dGTP, an adjusted amount of dTTP and dd*TP and a DNA polymerase enzyme.

Heterocycles other than naturally occuring DNA heterocycles such as adenine, cytosine, guanine and thymine are incorporated into the universal terminator dd*TP. These alternate heterocycles have reduced hydrogen bonding and have preferences to hydrogen bond with all four bases. One suitable dd*TP is dideoxy inosine triphosphate, a purine. Dideoxy inosine triphosphate can generally incorporate in the place of all four bases. Suitable universal terminators are shown in formula 2 for dideoxy inosine triphosphate; formula 1 for 5-nitro indole analog and formula 3 for 3-nitro pyrrole analog, where TPO is the triphosphate.

In FIG. 2, there is shown another embodiment B26A of gel electrophoresis having a negative-potential buffer for the A channel indicated generally at B29A, a gel electrophoresis channel for A terminated DNA indicated at B27A and a positive potential buffer for the channel indicated at B31A. This embodiment is intended to provide a small diameter cylindrical gel for each channel so as to permit better temperature control and thus control migration rate and reduce diffusion caused by temperature gradients such as may occur across a thicker slab gel.

For this purpose, the channel B27A includes a 0.01 to a 1 millimeter inner diameter glass column such as a chromatographic columm indicated at 33 with a gel inside of it. The gel may be cross-linked acrylamide or a non-crosslinked matrix. The column 33 is of sufficient length to separate the DNA.

At one end of the channel B27A is the buffer B29A adapted to provide a buffer solution in a surrounding cup shaped container 45, which buffer extends over the entering end 37 and contains within it a negative voltage electrode 47. At the exit end, there is similarly mounted a buffer compartment 51 containing buffer which is grounded by an electrode 53 and immerses in buffer the exit end 35 of the gel column B27A. It may be shaped with a reducing orifice ending in a micro-orifice 55 at its lower end to permit the flow of buffer therethrough containing DNA which emerges from exit end 35 for detection. To supply new buffer, a buffer reservoir 57 is connected through a pump 59 to the top of the buffer 51.

In FIG. 3, there is shown still another embodiment C26A which includes capillary columns 61 and 63 as commonly used in capillary electrophoresis. These columns may be filled with buffer solution rather than a gel and be used for electrophoresis. The bands of A, G, C or T type bases might flow through a different one of multiple parallel capillaries, or they might flow together through only one capillary.

The separation path such as gel channels or capillary tube length should be no longer than two meters for range of lengths of DNA for 50 to 10,000 or more bases. However, as the range of DNA lengths increase, the time required increases. Also, the time required for each separation is in the range of from ½ second to 5 minutes for each added base of length separation.

In the operation of sequencing DNA, DNA strands with bases above 100 in number are marked with one or more fluorescent molecules and separated in accordance to the size of the fragment. The bands are then detected by light.

To separate the fragments, the marked DNA fragments are electrophoresed through gel or liquid in one or more channels or columns. The DNA fragments separate in accordance with their length during electrophoresis. Thus the fastest migrating fraction is the fragment which is synthesized to the first base closest to the primed end of the strand and, since in the preferred embodiment, the channels are separate, it is known from the channel which

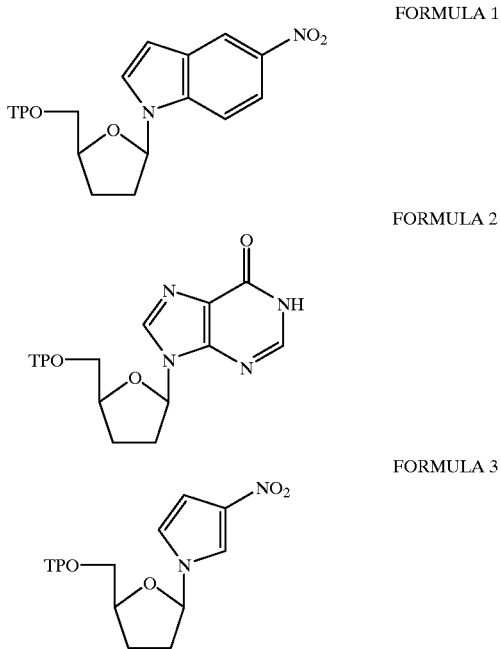

FORMULA 1

FORMULA 2

FORMULA 3 base A, G, C or T is the first one in the sequence. The next band in time in the gel is the fragment which is one base longer than the first one since it encompasses both the first base and the second one from the primed end of the DNA strand. Similarly, the third fragment to form a band during electrophoresis encompasses the first three base units and so on.

Because a large number of bases are used, there is a large number of varying length fragments and the amount of fragments in each band is relatively low. Thus, the gel and the field must be selected to provide a band having low diffusion, high concentration density and adequate separation for detection. The gel slab or capillary is sufficently long such that the first bands to be moved completely through the gel are fully resolved while the last bands are unresolved in a continuous process. More specifically, at least 10 percent of the bands are resolved and electrophoresed through the gel while the least mobile bands are yet unresolved near the entrance end of the gel.

The sequencing of far red or near infrared fluorescence labeled DNA and the detection of the DNA after irradiation by far red or near infrared light from a laser diode is accomplished using a far red or near infrared label prepared for this purpose and either directly attached to the DNA primer oligonucleotides or deoxynucleotides or the universal terminator. In this specification the word "infrared" will be used at times to include far red wavelengths (600–700 nm) and near infrared (700–3000 nm). The strands of DNA are continuously electrophoresed and identified for DNA sequencing.

The strands are marked with fluorescent labels that have their maximum fluorescense and their maximum absorbance at wavelengths of light in the far red or near infrared region. The strands are irradiated with light in the far red or near infrared region from a laser diode and the light emitted from the fluorescent labels is detected and used to obtain information about the DNA strands. The detector includes a light sensor which is preferably an avalanche photodiode sensitive to the far red or near infrared light emission of the marker. It may include a filtering system having a pass band suitable for passing selectively the optimum emission of the fluorescent marker to the light sensor.

To mark the DNA strand, a dye is synthesized having the desired properties or a known dye is modified. In the preferred embodiment a novel dye having the preferred absorbance spectrum, high molar absorptivity and fluorescence properties, and at least one reactive group enabling coupling to DNA primers, deoxynucleotides or terminators is synthesized.

The dye is synthesized or modified from a known dye or selected from commercially available sources to have an absorbance band and an emission band within the desired region. In the preferred embodiment this region is a region encompassing the far red or near infrared region when attached to a primer oligonucleotide, deoxynucleotide or universal terminator. The dye should provide high quantum yield in an optical band selected to reduce background fluorescence noise. The preferred dyes for many applications calling for the labeling of biomolecules are cyanine dyes having an NCS (isothiocyanate) group on the dye that may react with the primary amine group of the biomolecule to form a thiourea linkage or having NHS esters or hydroxyl groups or carboxyl groups for the purpose of reacting with the biomolecule to form linkages.

In the preferred embodiment, cyanine dyes are synthesized. The preferred dyes are pentamethine or heptamethine cyanines which efficiently absorb light having wavelengths in the region of 630 to 900 nm (nanometers) (maximum absorbance wavelength). This wavelength is suitable for reducing background fluorescence in DNA sequencing and corresponds to the radiation of diode lasers made of such materials as GaAlAs, GaAs, InGaAlP, GaInP, AlGaAs, AlGaInP, GaAlP, InGaAsP, GaInP/AlInP, or GaInP/AlGaInP. The GaAlAs diode, for example, emits at 780–800 nm and is used for irradiating the gel electrophoresis slab sandwich, column, or capillary used for DNA sequencing. Formulas 4–6 are typical synthesized dyes and formula 7 is a suitable modified dye.

Formula 4 shows synthesized cyanine dyes having NCS (isothiocyanate) as a reactive group for attachment of a biomolecule. In this embodiment, when X is H, the maximum absorbance wavelength is 787 nm in methanol and 801 nm in DMSO, and the maximum emission wavelength is 807 nm in methanol and 818 nm in DMSO. When X is —$OCH_3$, the maximum absorbance wavelength is 786 nm in methanol and the maximum emission wavelength is 806 nm methanol. In both cases, the quantum yield is greater than 15 percent.

Formula 5 shows synthesized cyanine dyes which have a high quantum yield in methanol around 35 percent. When R is ethyl or sulfonatobutyl and n is either 1 or 2, the maximum absorbance wavelength is between 762 and 778 nm. Depending on the solvent, the maximum emission wavelength is between 782 and 800 nm.

In the synthesized dye represented by formula 6, the maximum absorbance wavelength is between 773 and 778 nm depending on the solvent and the maximum emission wavelength is between 789 and 806 nm depending on the solvent. The quantum yield is between 25 percent and 35 percent depending on the solvent.

A new series of dyes is obtained by modifying a commercial dye, IR-144 shown as formula 7, with R being —$CH_2$—$CH_3$. The series of dyes, obtained by changing R, is close to having the desired wavelength of maximum fluorescence. The wavelength of maximum absorbance may be modified by changing the functional group R. The unmodified dye may be obtained from Laboratory and Research Products Division, Eastman Kodak Company, Rochester, N.Y., 14650. It is advertised in Kodak publication JJ-169.

In the preferred embodiment, the fluorescence maximum wavelength is about 819 nanometers and the detector is adjusted to receive this wavelength and not others by appropriate filtering. The absorbance maximum is selected to be different and to correspond to the preferred available laser diode emission. For example, in this formula, R may be any of the following four groups, depending on the desired wavelength of the absorbed light, which are:

(1) —$CH_2$—$CH_2$—OH for an absorbance wavelength of 796 nanometers;

(2) —$CH_2$—$CH_2$—$CH_2$—OH for an absorbance wavelength of 780 nanometers;

(3) —$CH_2$—$CH_2$—$CH_2$—$CH_2$—$CH_2$—$CH_2$—OH for an absorbance wavelength of 745 nanometers; and (4) —$CH_2$—$CH_2$—O—$CH_2$—$CH_2$—O—$CH_2$—$CH_2$—OH for an absorbance wavelength of 790 nanometers.

In FIG. 4, there is shown an embodiment E10 of sequencing system having a central system 120, a plurality of remote stations, two of which are shown at 122A and 122B and a DNA fluorescent marking system 121. The DNA fluorescent marking system 121 includes means for labeling identical strands of DNA

FORMULA 4

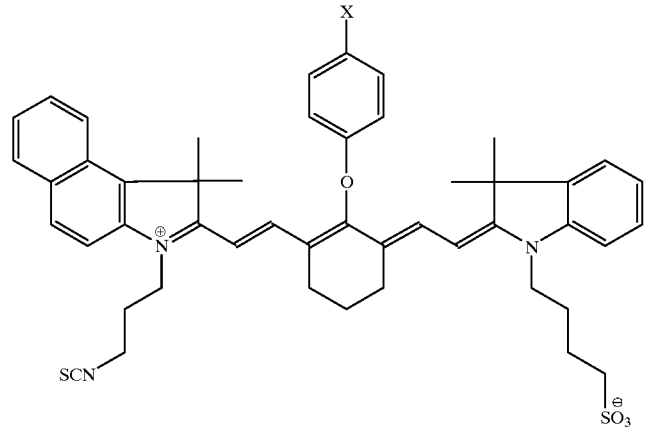

FORMULA 5

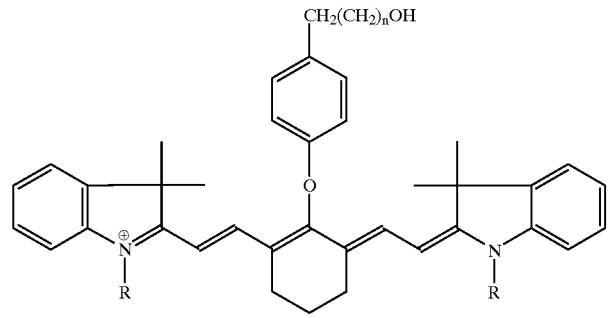

-continued

FORMULA 6

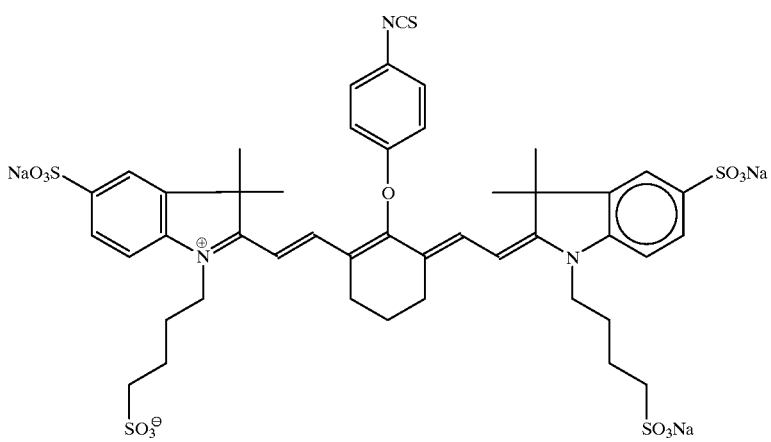

FORMULA 7

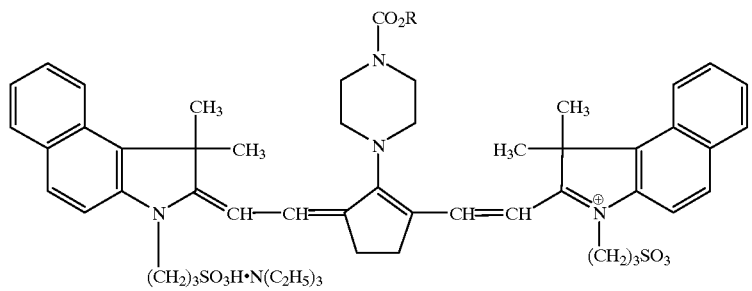

and a DNA preparation system. In this preparation process, strands are separated into four aliquots. The strands in a given aliquot are synthesized to any base belonging to one or more of the four base types, which are adenine, guanine, cytosine and thymine (hereinafter A, G, C and T). The adenine-, guanine-, cytosine- and thymine-terminated strands are then electrophoresed for separation. The rate of electrophoresis indicates the DNA sequence.

The fluorescent markers are attached to the identical strands of more than 100 bases in a container. The fluorescent markers may be attached to DNA primer molecules or to deoxynucleotide triphosphates used in the synthesis of the DNA strands or to dideoxynucleotide triphosphates which terminate synthesis of the DNA strands or to universal terminators. Single or multiple fluorescent markers may be attached to the DNA fragments. They must be of such a size and have such chemical characteristics as to not obscure the normal differences in the mobilities between the different fragments due to terminations at different ones of the adenine, guanine, cytosine and thymine bases and be able to be easily detected.

The DNA fluorescent marking system 121 communicates with the central system 120 as well as the remote stations 122A and 122B. The central system 120 includes a separating system and a detection and processing system to separate the strands by length with each fragment being terminated at a different one of the A, T, G and C groups. The separating system, which sequences strands by length, communicates with the detection and processing system which analyzes the fragments by comparison of the progress of each band of DNA fragments along the gel with the other bands to derive information about the sequence of the DNA.

The separating system continuously sequences strands of DNA, and for this purpose, the preferred embodiment includes at least four electrophoresis channels, each adapted to receive fluorescently labeled DNA strands having at one end a universal terminator substituted for a base of a given type. Each of the channels has a gel path and electrical field across it identical in its characteristics to the gel path of the other channels and electrical fields across the other channels. The bands are detected in a manner that indicates their mobility in the gel to indicate the sequence of the A, G, C and T strands of different lengths.

The detection and processing system includes a scanning apparatus having a light source, such as a laser diode or light-emitting diode or other suitable source that emits light in the optimum absorbance spectrum of the marker. The light may be split by the use of fiber. In the preferred embodiment, the light source is a laser diode that irradiates the channels with far red or near infrared light having a wavelength that matches the absorbance region of the marker. The detector includes a light sensor that is preferably an avalanche photodiode that is sensitive to the far red or near infrared light emission of the marker. It may include a filtering system having a pass band suitable for passing selectively the optimum emission of the fluorescent marker to the light sensor.

The photodiode, photomultiplier or other light sensor selectively detects the fluorescence using techniques which enhance the signal/noise ratio. One technique is to modulate the laser source by pulsing the electrical current driving the laser and detect light in sequence with the emitted light by connecting the output signal from the sensor with a lock-in amplifier that is sequenced with the pulsed laser light. Another technique is the use of laser pulses which are less than five nanoseconds time duration, with detection in a time window. The length of such window and its delay from the pulse are optimized to discriminate against background fluorescence as well as scattered laser light.

Another technique is the use of sinusoidally modulated laser pulses combined with phase modulation discrimination.

To determine the sequence of strands, the processing system includes means for correlation between the channel in which the fluorescent light is detected with the time of detection and means for indicating: (1) which of the base types, A, G, C or T, the termination is associated with; and (2) the time sequence of separation of each strand in each channel of the electrophoresis gel.

To use the apparatus to sequence DNA strands, identical DNA strands are normally formed of a length greater than 100 bases. In one embodiment, the strands are marked by a suitable marker. The strands are divided into four aliquots and the strands within each aliquot are synthesized to any base belonging to a specific base type. These four aliquots are then electrophoresed through identical channels to separate strands so that the shorter strands are resolved towards the end of the gel prior to resolution of the longer strands, which still are near the entrance end of the gel. In another embodiment, the strands are divided into four aliquots and synthesized to a given base, with marking ocurring during termination of synthesis. The same marker may be used for all four aliquots and separation may be performed as described above or a different marker may be used for each different termination group of the A, T, C and G groups so as to process in a single channel for a complete sequence. This occurs in a continuous process so a substantial number of different length strands may be resolved in a relatively short gel. This methodology takes advantage of time-resolved bands, as opposed to the limitations of spatial-resolved bands.

The gel size, electric field and DNA mobilities are such that the more mobile bands are fully resolved while the less mobile bands are yet unresolved in a continuous process such that at least ten percent of the bands have been resolved by electrophoresis in the gel while the less mobile bands which are near the entrance end of the gel are not fully resolved. These less mobile bands become resolved little by little over time in a continuous fashion without interruption of the movement of these bands through the gel. The markers are detected by transmitting far red or near infrared light to fluorescently marked DNA strands which may be at the same far red or near infrared wavelength or at different far red or near infrared wavelengths depending on the embodiment of separation technique.

The remote stations 122A and 122B each are able to perform the sequencing but some portions of data processing can only be performed by the central station 120. It may supply data to the remote stations, such as 122A and 122B, to which it is electrically connected and receive data from them. With this arrangement, the central sequencing system 120 may cooperate with one or more of the remote stations, such as 122A and 122B, for increased capability such as increased number of channels. Each unit may control the parameters used in sequencing, such as the electrophoresis potential or the like.

In FIG. 5, there is shown a simplified view of the remote station 122A having a cabinet housing 130, a front cover 132, a liquid crystal display readout 134, a high voltage warning light 136 and a plurality of function keys 138. In FIG. 5, the remote station 122A is shown closed. However, the front cover 132 may be removed to expose an electrophoresis section. The potential applied across the gel may be set and different data readouts may be selected either from the analysis provided within the central system 120 (FIG. 4) or values from within the remote station 122A using the function key pad 138 and the selected data displayed on the liquid crystal display readout 134 prior to and/or after selection.

In FIG. 6, there is shown a sectional view of a portion of the remote station 122A taken through section lines 6–6 of FIG. 5 having an electrophoresis section 140, a scanning section 142, an electrophoresis power supply 144, a system power supply section 144A, an analog board 146 and a digital board 148. The electrophoresis section 140 is positioned near the front of the cabinet and a portion of it is adapted to be scanned by the scanning section 142 in cooperation with circuitry on the analog board 146 and the digital board 148. All of the apparatus are electrically connected to the power supply section 144A for such operation.

To separate different DNA fragments into bands, the electrophoresis section 140 includes a gel sandwich 150, an upper buffer assembly 152, a support assembly 154, and a lower buffer assembly 151 positioned to enclose the bottom of the gel sandwich 150. In the embodiment of FIG. 6, the gel sandwich 150 is held vertically and its temperature is controlled during operation. Bands are separated by applying voltage to the upper buffer assembly 152 and lower buffer assembly 151 and scanned by the scanning section 142.

To support the gel sandwich 150, the support assembly 154 includes a pair of upper side brackets and lower side brackets 160 and 162 (only one of each pair being shown in FIG. 6), an apparatus support plate 168, a temperature control heating plate 164 and a plastic spacer, shown at 166A–166C, in FIG. 6. The entire structure is supported on the apparatus support plate 168 which mounts the upper and lower side brackets 160 and 162.

The upper and lower side brackets 160 and 162 are each shaped to receive a pin such as 161 and 167 (FIG. 9) extending from a gel sandwich such as the gel sandwich 150 and thus hold the gel sandwich in place on one side in juxtaposition with the scanning section 142. The pin 167 (FIG. 9) on the side of the sandwich opposite to the pin 161 (FIG. 9) fits into a corresponding one of two brackets 163 and 160 (FIG. 9) so that the gel sandwich can be hooked in place. The other two brackets 165 and 162 are positioned to receive the pins of other length gel sandwiches with the lower bracket 162 receiving pins of shorter vertical length sandwiches than the upper bracket 160. Even longer gel sandwiches can be mounted by substituting a longer heating plate for the heating plate shown at 164.

The spacers as shown as 166A–166C space the temperature control heating plate 164 from the apparatus support plate 168 and maintain it at a constant selected temperature above ambient temperature. In the preferred embodiment, the temperature is maintained at 45–50 degrees Centigrade and should be maintained in a range of 30 degrees to 80 degrees.

The scanning section 142 includes a laser diode assembly (not shown in FIG. 6), a microscope assembly 172, a photodiode section 174 and a scanner mounting section 176. The laser diode assembly (not shown in FIG. 6) is positioned at an angle to an opening in the apparatus support plate 168 and the heating plate 164 so that light impinges on the gel sandwich 150 to cause fluorescence with minimum reflection back through the microscope assembly 172.

To receive the fluorescent light, the microscope assembly 172 is focused on the gel sandwich 150 and transmits fluorescent light emitted therefrom into the photodiode section 174 which converts it to electrical signals for transmission to and processing by the analog and digital boards 146 and 148 which may provide further analysis of data. The scanning section 142 moves along a slot in the apparatus support plate 168 which is mounted to the scanner mounting section 176 during this operation in order to scan across the columns in the gel sandwich 150.

The scanner mounting section 176 includes a mounting plate 180, a bearing plate 182, a stepping motor 184, a slidable support 186 and a belt and pully arrangement 185, 188A and 188B. The mounting plate 180 is movably mounted to the apparatus support plate 168 through a frame member and supports the elongated bearing plate 182, the stepping motor 184 and two pulleys 188A and 188B. The elongated bearing plate 182 extends the length of the gel sandwich 150.

To permit motion of the laser diode assembly (not shown) and microscope assembly 172 with respect to the gel sandwich 150, the slidable support 186 supports the microscope assembly 172 and laser diode assembly and slidably rests upon the bearing plate 182. An output shaft 183 of the stepping motor 184 drives a pulley 188B through pulley 188, belt 185, and pulley 188A and the pulley 188B drives a belt (not shown) that is clamped to the slidable support 186 to move it the length of the gel sandwich 150 during scanning by the laser diode and microscope assembly 172 which rest upon it. The stepping motor 184 under the control of circuitry in the digital board 148 moves the pulley 188B to move the belt (not shown) and thus cause scanning across the gel sandwich 150.

As shown in this view, the electrophoresis power supply 144 is electrically connected to buffer in the upper buffer assembly 152 through an electrical connector 194 and to the lower buffer assembly 151 through a connector not shown in FIG. 6.

The upper buffer assembly 152 includes walls 197 forming a container to hold a buffer solution 195 and a cover 199 formed with a lip to fit over the walls 197 from the top and containing a downwardly extending flat member spaced away from the side walls and holding a conductor 211. The conductor 211 is electrically connected to the source of power through connector 194 which is mounted to the top of the cover 199 to permit electrical energization of the buffer solution 195.

The bottom buffer assembly 151 includes enclosed walls 201 defining a container for holding a buffer solution 203 and a cover 205 closing the container 201 and having a downwardly extending portion 213 extending into the buffer solution 203 for supporting a conductor 207 for applying energy to the bottom buffer solution 203. The gel sandwich 150 extends downwardly into the buffer solution 203 and upwardly into the buffer solution 195 to permit the electrical contact for electrophoresis. An "O" ring 197B provides a seal for the upper buffer assembly 152 so that the buffer solution 195 does not empty out of the upper buffer assembly 152.

Figure 7:
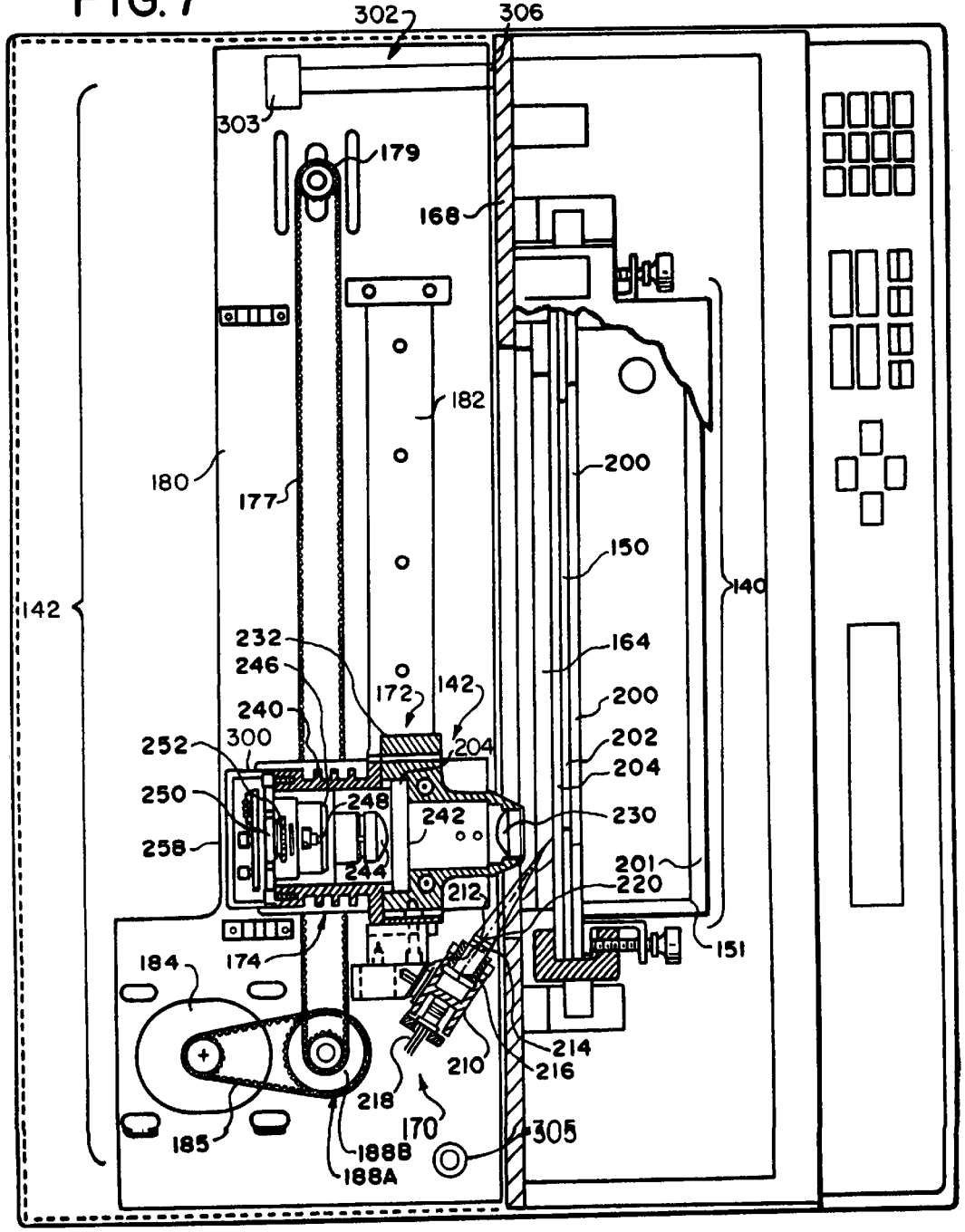
FIG. 7 is a sectional view of a portion of FIG. 5 taken through lines 7—7.

In FIG. 7, there is shown a sectional view taken through lines 7–7 of FIG. 5 showing a portion of the electrophoresis section 140, a portion of the scanning section 142 (indicated twice in FIG. 7 for clarity) and the electrophoresis power supply section 144 (FIG. 6) mounted together to illustrate, from a top view, the arrangement of the apparatus support plate 168, the heater plate 164, the gel sandwich 150, a laser diode assembly 170, a microscope assembly 172 and a photodiode assembly 174. The heater plate 164 and apparatus support plate 168 have slots running in a horizontal direction orthogonal to the lanes of DNA in the electrophoresis section 140 sized to receive the ends of a laser diode assembly 170 and the microscope assembly 172 for scanning thereof.

To cooperate with the separation and scanning of DNA bands, the gel sandwich 150 includes a front glass plate 200, a gel section 202 and a rear glass plate 204 mounted in contact with the heater plate 164 and having a section exposed for scanning by the laser diode assembly 170 and the microscope assembly 172. The rear glass plate 204 contacts the heater plate 164 and is separated from the front glass plate 200 by the gel section 202 within which DNA separation takes place. The front and rear glass plates 200 and 204 may be any type of glass but are preferably soda lime which has low fluorescence in the far red and near infrared regions and is prepared by a process that provides optically flat surfaces without grinding.

To transmit light to the gel sandwich 150, the laser diode assembly 170 includes a housing 210, a focusing lens 212, a narrow band pass filter 214, a collimating lens 216 and a laser diode 218. The laser diode 218 emits far red or near infrared light which is collimated by the laser collimating lens 216 and filtered through the narrow band pass filter 214. This light is focused by the focusing lens 212 onto the gel sandwich 150. Preferably, the point of focus on the gel section 202 of the gel sandwich 150 lies along or near the central longitudinal axis of the microscope assembly 172 and the photodiode assembly 174.

The thickness of the glass plates and the gel, the position of the laser and microscope assembly and thus the angle of incidence and angle of reflection of the light from the laser and to the microscope assembly 172 are chosen, taking into consideration the refractive index of the gel and glass and the thickness of the glass plates and the gel, so that the light from the laser is maximally transmitted to the gel. The light from the laser is not directly reflected back because the angle of incidence to normal is equal to the Brewster's angle at the first interface and is such as to impinge on the markers with full intensity after refraction but not be reflected by the first surface of the gel sandwich 150 into the microscope assembly 172 and the microscope assembly 172 views those markers that fluoresce in its line of sight.

To maintain temperature control over the laser diode, the housing 210: (a) is coupled to a heat sink through a thermal electric cooler 220, and (b) encloses the focusing lens 212, narrow band pass filter 214, collimating lens 216 and laser diode 218; and (c) accommodates the electrical leads for the diode.

To receive and focus light emitted by fluorescent markers from the gel section 202 in response to the light from the laser diode assembly 170, the microscope assembly 172 includes a collection lens 230, a housing 232, and a focusing motor. The microscope assembly 172 is adapted to be positioned with its longitudinal axis centered on the collection lens 230 and aligned with the photodiode assembly 174 to which it is connected. For this purpose, the housing 232 includes a central passageway in which are located one or more optical filters (not shown) with a pass band matching the emission fluorescence of the marked DNA strands. With this arrangement, the collection lens 230 receives light from the fluorescent material within the gel section 202 and collimates the collected light for optical filtering and then transmission to the photodiode assembly 174.

To generate electrical signals representing the detected fluorescence, the photodiode assembly 174 includes a housing 240 having within it, as the principal elements of the light sensor, an inlet window 242, a focusing lens 244, a sapphire window 246 and an avalanche photodiode 248. To support the avalanche photodiode 248, a detector mounting plate 250 is mounted within the housing 240 to support a plate upon which the avalanche photodiode 248 is mounted. The inlet window 242 fits within the housing 240 to receive light along the longitudinal axis of the photodiode assembly 174 from the microscope assembly 172.

Within the housing 240 of the photodiode assembly 174, the sapphire window 246 and avalanche photodiode 248 are aligned along the common axis of the microscope assembly 172 and the photodiode assembly 174. The focusing lens 244 focuses light transmitted by the microscope assembly 172 onto a small spot on the avalanche photodiode 248 for conversion to electrical signals. A thermoelectric cooler 252 utilizing the Peltier effect is mounted adjacent to the detector mounting plate 250 to maintain a relatively cool temperature suitable for proper operation of the avalanche photodiode 248.

As best shown in this view, the stepping motor 184 rotates the belt 185 to turn the pulley 188A, which, in turn, rotates pulley 188B. The pulley 188B includes a belt 177 extending between it and an idler pulley 179 and is attached at one location to the slideable support 186 (FIG. 6) to move the scanning microscope and laser lengthwise along the gel sandwich 150 for scanning purposes. The motor 184, by moving the carriage back and forth accomplishes scanning of the gel sandwich 150.

Figure 8:
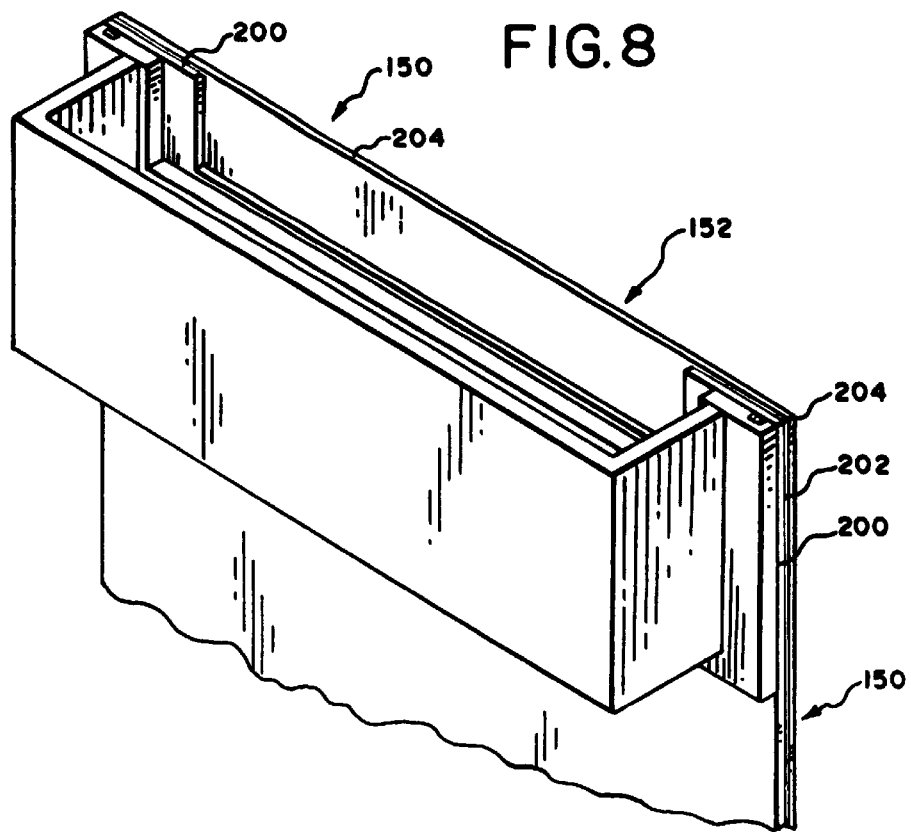
FIG. 8 is an exploded perspective view of a portion of the embodiment of FIG. 7.

In FIG. 8, there is shown a fragmentary perspective view of the gel sandwich 150 and the upper buffer assembly 152 mounted to each other showing the outer glass plate 200 cut away from the rear glass plate 204 to expose the gel section 202 to buffer solution within the upper buffer assembly 152. With this arrangement, DNA samples may be pipetted between the glass plates 200 and 204 and moved downwardly by electrophoresis beyond the upper buffer assembly 152 and through the gel sandwich 150 to the bottom buffer (not shown in FIG. 8).

Figure 9:
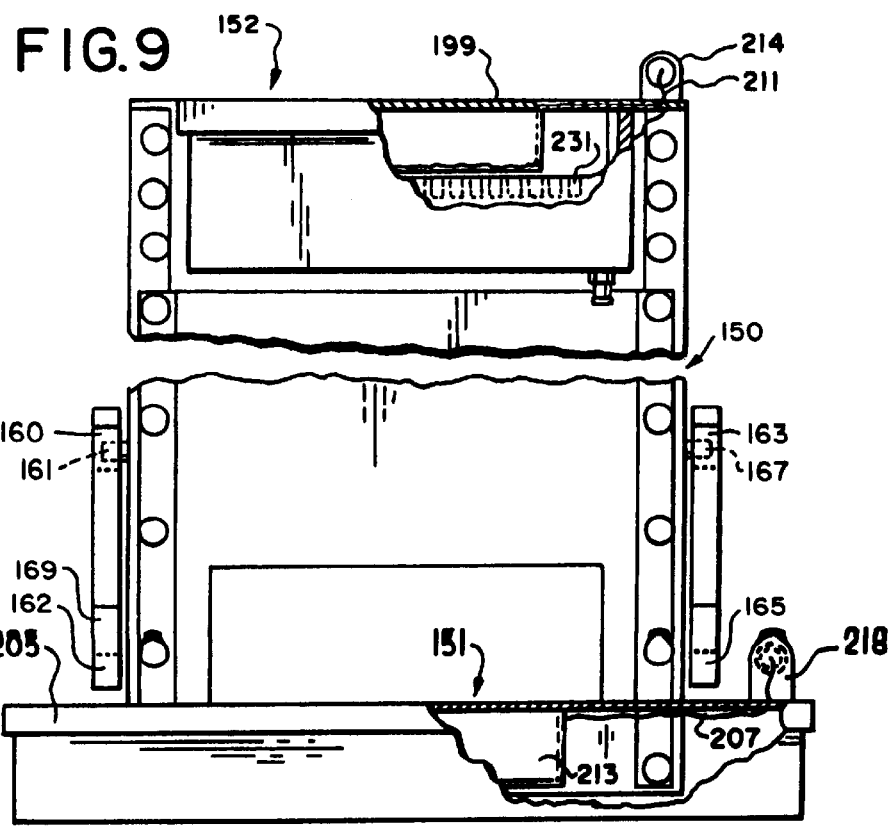
FIG. 9 is an enlarged view, partly broken away, of a portion of the embodiment of FIG. 7.

In FIG. 9, there is shown a broken away view of the gel sandwich 150 illustrating the upper buffer assembly 152 and the lower buffer assembly 151 connected to it at each end. As shown in this view, the cover 199 includes a connecting post 214 which receives the elongated flexible conductor 211 for connection to the downwardly extending portion of the cover 199 into the buffer compartment. This flexible conductor has sufficient length to accommodate different lengths of gel sandwiches that cause the upper buffer assembly 152 to be at different elevations. In another embodiment, the length of conductor 211 is the same for the different lengths of gel sandwiches in that this cover 199 is raised or lowered depending on the gel length. To accomodate electrical connection in this embodiment, either the connecting post 214 mates with one of a series of mounting connectors located at different vertical positions on the apparatus support plate 168 (FIG. 6) or the connecting post 214 mates with a flexible extension cable that electrically connects the connecting post 214 with a mounting connector.

As best shown in this view, a plurality of side brackets 160, 163, 165 and 169 are mounted to the apparatus support plate 168 (FIG. 6) to receive pins 161 and 167 extending from the sides of the gel sandwich 150 to support the gel sandwich in place. The pins 161 and 167 extend from opposite sides of the gel sandwich at the same elevation and the brackets 160, 163, 165 and 169 are mounted in pairs to the apparatus support plate 168 (FIG. 6) with each pair being at a different elevation and each bracket of a pair of brackets being positioned on the opposite side of the gel sandwich from the other bracket of the same pair to support different sizes of gel sandwichs at a location that provides balance to them.

The upper and lower side brackets 160 and 162 on one side of the gel sandwich and the upper and lower side brackets 163 and 165 on the opposite side are each shaped to receive a pin such as 161 and 167 (FIG. 9) extending from the gel sandwich 150 and thus hold the gel sandwich in place on one side in juxtaposition with the scanning section 142 (FIGS. 6 and 7). The pin 167 on the side of the sandwich opposite to the pin 161 fits into a corresponding one of the two brackets 163 and 165 so that the gel sandwich can be hooked in place. For longer gel sandwiches, the pin 167 fits into bracket 163 while for shorter gel sandwiches the pin 167 fits into bracket 165. The other of the two brackets 160 and 169 are positioned to receive the pin located on the opposite side of the gel sandwich such that the lower bracket 169 receives the pin of shorter vertical length gel sandwiches and the upper bracket 160 receives the pin of longer vertical length gel sandwiches. Even longer gel sandwiches can be mounted by substituting a longer heater plate for the heater plate shown at 164 (FIG. 6). As best shown in this view, recesses 231 extend downwardly into the gel to receive DNA sample from a pipette and thus form channels for electrophoresing.

To form an electrical connection through the gel sandwich 150 from the upper buffer assembly 152 to the lower buffer assembly 151, a connecting post 218 is connected to the cover 205 of the lower buffer assembly 151 for receiving the conductor 207 (FIG. 6) which extends downwardly to the downwardly extended plate 213 and into the buffer solution.

Figure 10:
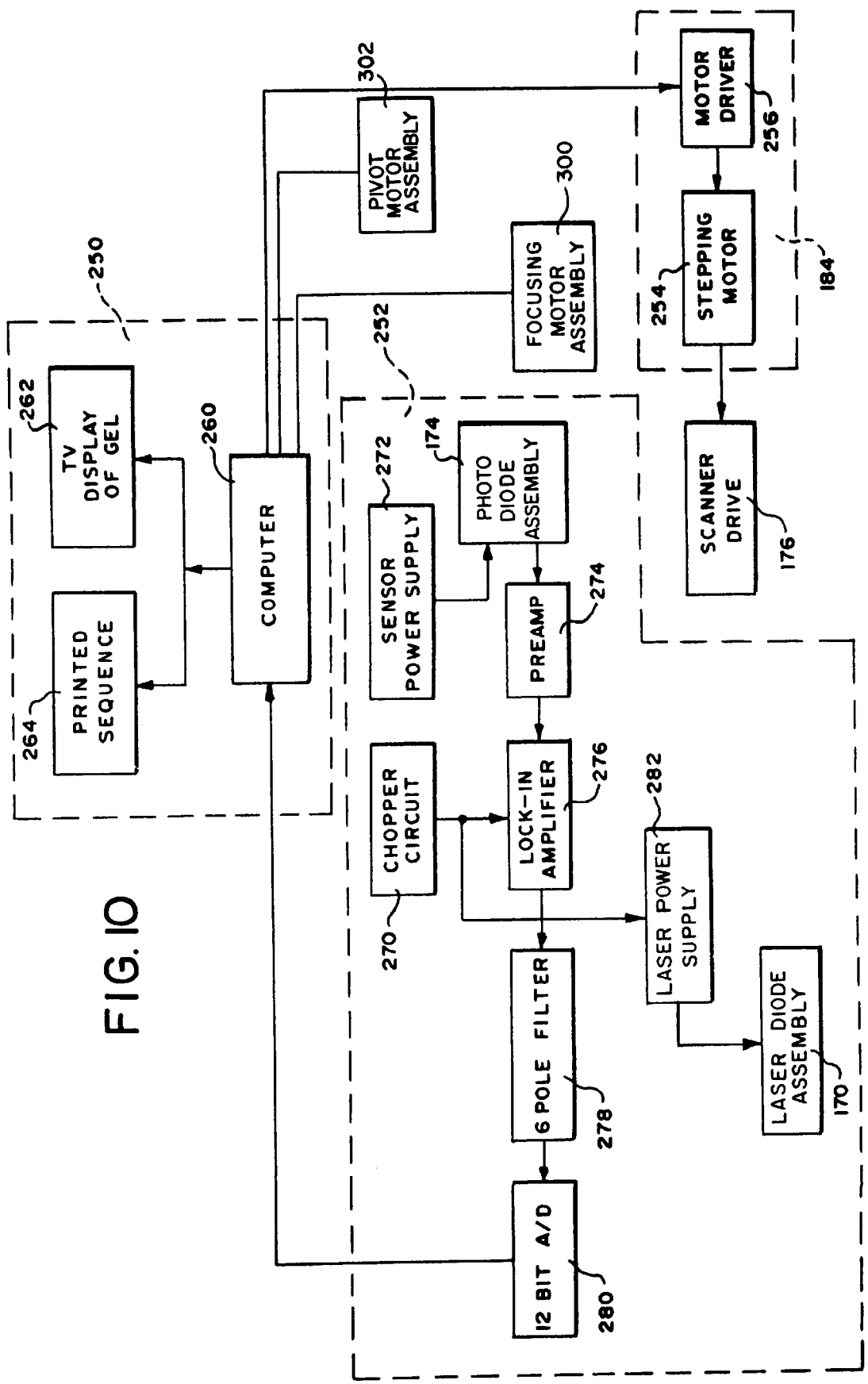
FIG. 10 is a block diagram of a circuit that may be used for coordination of a sensor, scanner drive and laser used in the embodiment of FIG. 7.

In FIG. 10, there is shown a block diagram of the circuitry used to control the remote station 122A of the embodiment of FIG. 5 having a control, correlation and readout section 250, a scanner drive 176, the motor assembly 184 for moving the scanner drive 176, the sensing configuration 252 and the focusing motor assembly and pivot motor assemby controls 300 and 302 respectively.

The sensing configuration 252 includes the laser diode assembly 170 and the photodiode assembly 174 which receives signals, removes some noise, and transmits the signals for display and readout in the control, correlation and readout section 250. At the same time, the scanner drive 176 and motor for the scanner drive 184 receive signals from the control, correlation and readout section 250 to control the motion of the sensor back and forth across the gel sandwich. This overall configuration is not part of the invention of this application except insofar as it cooperates with the sensing configuration 252 to scan the DNA and determine its sequence in accordance with the embodiments of FIGS. 5–10.

To drive the laser diode assembly 170 and the microscope assembly 172 (FIGS. 6 & 7) and the photodiode assembly 174 from position to position, the motor assembly 184 includes a stepping motor 254 and a motor driver 256. The motor drive 256 receives signals from the control correlation and readout section 250 and actuates the stepping motor 254 to drive the scanner drive 176. The scanner drive 176 is mechanically coupled to the stepping motor 254 through a belt and pulley arrangement for movement back and forth to irradiate and sense the electrophoresis channels on the gel sandwich 150 (FIG. 6). The stepping motor 254 and motor driver 256 are conventional and not themselves part of the invention.

To correlate the scan with received signals and provide a display of them, the control, correlation and readout system 250 includes a computer 260 which may be any standard microprocessor, a television display or cathode ray tube display 262 and a printer 264 for displaying and printing the results of the scans. Data, after being processed in sensing configuration 252 is supplied to the computer 260 for correlation with the position of the scanner drive 176 as controlled by the computer 260 and display 262.

To sense data, the sensing configuration 252 includes in addition to the laser diode assembly 170 and the photodiode assembly 174, a chopper circuit 270, a sensor power supply 272, a preamplifier 274, a lock-in amplifier 276, a 6-pole filter 278, a 12-bit analogue to digital converter interface circuit 280 and a laser power supply 282. The photodiode assembly 174 receives light from the laser diode assembly 170 after it impinges upon the gel sandwich 150 (FIG. 6) and transmits electrical signals through preamplifier 274 to the lock-in amplifier 276. The photodiode assembly 174 receives signals from the sensor power supply 272. The chopper circuit 270 provides pulses at synchronized frequencies to the lock-in amplifier 276.

The laser diode assembly 170 receives power from the power supply 282 which is controlled by the chopper circuit 270 so that the signal from the laser diode assembly 170 is in synchronism with the signal applied to the lock-in amplifier 276 so that the output from the lock-in amplifier 276 to the 6-pole filter 278 discriminates against unwanted signal frequencies. This signal is converted to a digital signal in the 12-bit analogue to digital converter 280 which serves as an interface to the computer 260.

Figure 11:
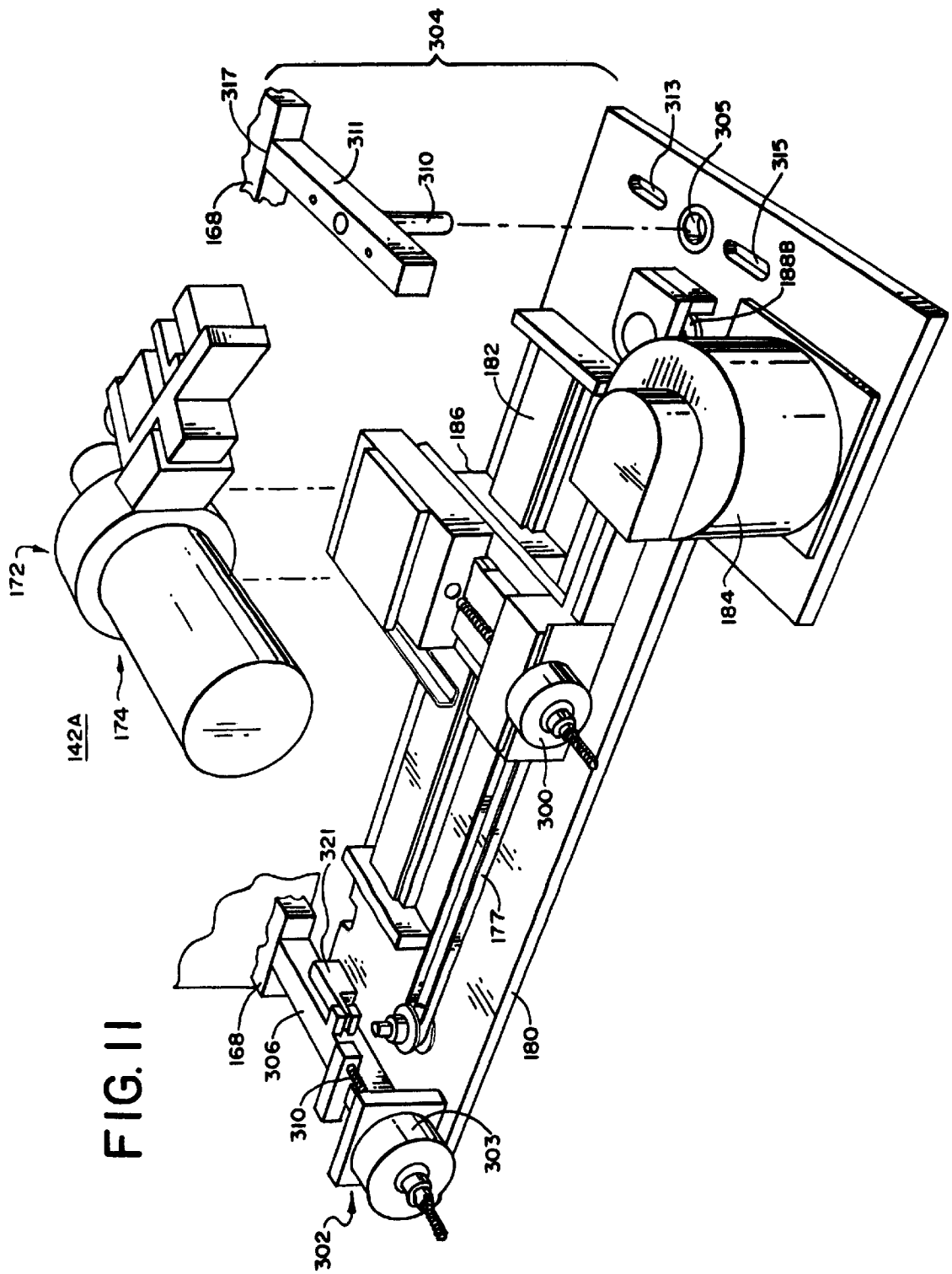
FIG. 11 is a perspective view from the top right side of another embodiment of scanning section usable in the DNA sequencing apparatus of FIGS. 4 and 5.

To maintain optical focus, the computer 260 is electrically connected to the pivot motor assembly 302 and the focusing motor assembly 300, which motor assemblies are able to adjust the microscope assembly 172 (FIGS. 6 and 7) to focus it and to adjust the location of the microscope with respect to the gel sandwich 150 by pivoting the support bed 180 (FIGS. 7 and 11). As will be better explained hereinafter, this permits a number of different focusing arrangements such as one in which the microscope is periodically refocused during an individual scan across the gel to maintain focus and one in which the distance between the gel sandwich and the path of travel of the microscope is adjusted with respect to each other so that during movement of the microscope as it scans, the focal point is maintained on the gel even though there was originally some non parallelism between the gel and the travel path of the microscope along the course of a scan. Of course both motors may be controlled simultaneously as better explained hereinafter.

In FIG. 11, there is shown a fragmentary, exploded top perspective view of another embodiment of scanning section 142A substantially the same as the scanning section 142 of FIGS. 6 and 7 in which the identical parts are indicated by the same reference numerals in each embodiment. As shown in this view, the scanning section 142A includes three motor assemblies, the stepping motor assembly (scan motor assembly) 184, the focusing motor 300 and a mounting plate pivot motor assembly 302 and a pivot assembly 304. The mounting plate pivot motor assembly 302 is only in the embodiment of scanning assembly 142A but the focusing motor 300 and stepping motor assembly 184 are in both the embodiment of scanning section 142 and the embodiment 142A. The motor assembly 184 operates in the same manner in both embodiments to drive the output shaft 183 (FIGS. 6 and 12) which in turn drives the slidable support 186 (FIG. 6) on the bearing plate 182 (FIGS. 6 and 7) through the belt 185 (FIGS. 6 and 12) and toothed belt 177.

The focusing motor assembly 300 is mounted for movement with the microscope assembly 172 and photodiode assembly 174 to focus the microscope assembly 172 directly into the gel to receive light directly from the fluorescent markers therein. This focusing may be done manually or automatically by focusing at points where there is no fluorescent emission from DNA markers in the gel. This is done by sensing the fluorescence of the two glass plates which have relatively high emission and causing the focusing to be between the two high emission glass plates and within the lower emission gel.

The pivot motor assembly 302 cooperates with the pivot assembly 304 to adjust the angle between the gel sandwich 150 (FIG. 6) and the mounting plate 180 so that the focus of the microscope assembly 172 can be set and the focal point remain within the gel section as the microscope assembly 172 moves in a horizontal scanning direction across the gel sandwich 150 (FIG. 6). The pivot motor assembly 302 cooperates in the focusing operation so that the microscope is focused at one point at one end of the gel sandwich 150 and then the microscope assembly 172 scans across to another widely separated point without changing the focus of the microscope lens.

After the microscope assembly 172 has moved to a new location, the pivot motor assembly 302 then moves the support bed 180 about the pivot point 305 with the motion being in a horizontal plane to adjust the angle in the vertical plane of the support bed 180 and gel sandwich 150 with respect to each other so that the plane of the gel sandwich 150 and the scan direction are parallel. The focus motor 300 then refocuses the microscope assembly 172 so that the focus point is the same at both extremes of a scan, thus permitting a continuous scan without the need to dynamically refocus the microscope. Of course either the gel sandwich or support for the microscope or both can be adjusted with minor modification of the equipment.

To permit adjustment of the horizontal scanning path of the microscope assembly 172, the pivot assembly 304 in the preferred embodiment includes an opening or eyelet at pivot point 305 with the pivot point 305 having a vertical axis perpendicular to the support plate 180, a cylindrical vertically oriented pivot pin 310 and a mounting housing 311 rigidly mounted to the pivot pin 310. The pivot pin 310 fits rotatably within the support bed 180 and the support bed 180 is movably bolted to the housing 311. The bolts (not shown in FIG. 11) have shanks that extend loosely through the openings 313 and 315 to permit movement between the support plate 180 and housing 311 to permit pivoting of the support bed 180 with respect to the housing 311. The housing 311, which is mounted at end 317, and the corresponding end of a support member 306 are mounted to the apparatus support plate 168 (FIG. 6) to movably support the two ends of the support bed 180 on the DNA sequencer frame.

To provide pivoting, the pivot motor assembly 302 includes the motor output shaft 319, biasing member 321 and support member 306 so that rotation of the motor 303 in one direction causes the motor output shaft 319 to push against the vertical apparatus support plate 168 (FIG. 6) to which it is movably mounted at one end to increase the angle, and rotation in the other direction pulls it to reduce the angle or releases it to be pulled by a biasing member 321 to move the bed forwardly to the plate 168 and decrease the angle. The support member 306 is mounted to the support plate 180 by bolts (not shown in FIG. 11) having their shanks fitting through slots similar to 313 and 315 that are large enough to permit pivoting. The support member 306 is mounted to vertical apparatus support plate 168 so that the support member 306 is supported to the frame of the DNA sequencer.

Figure 12:
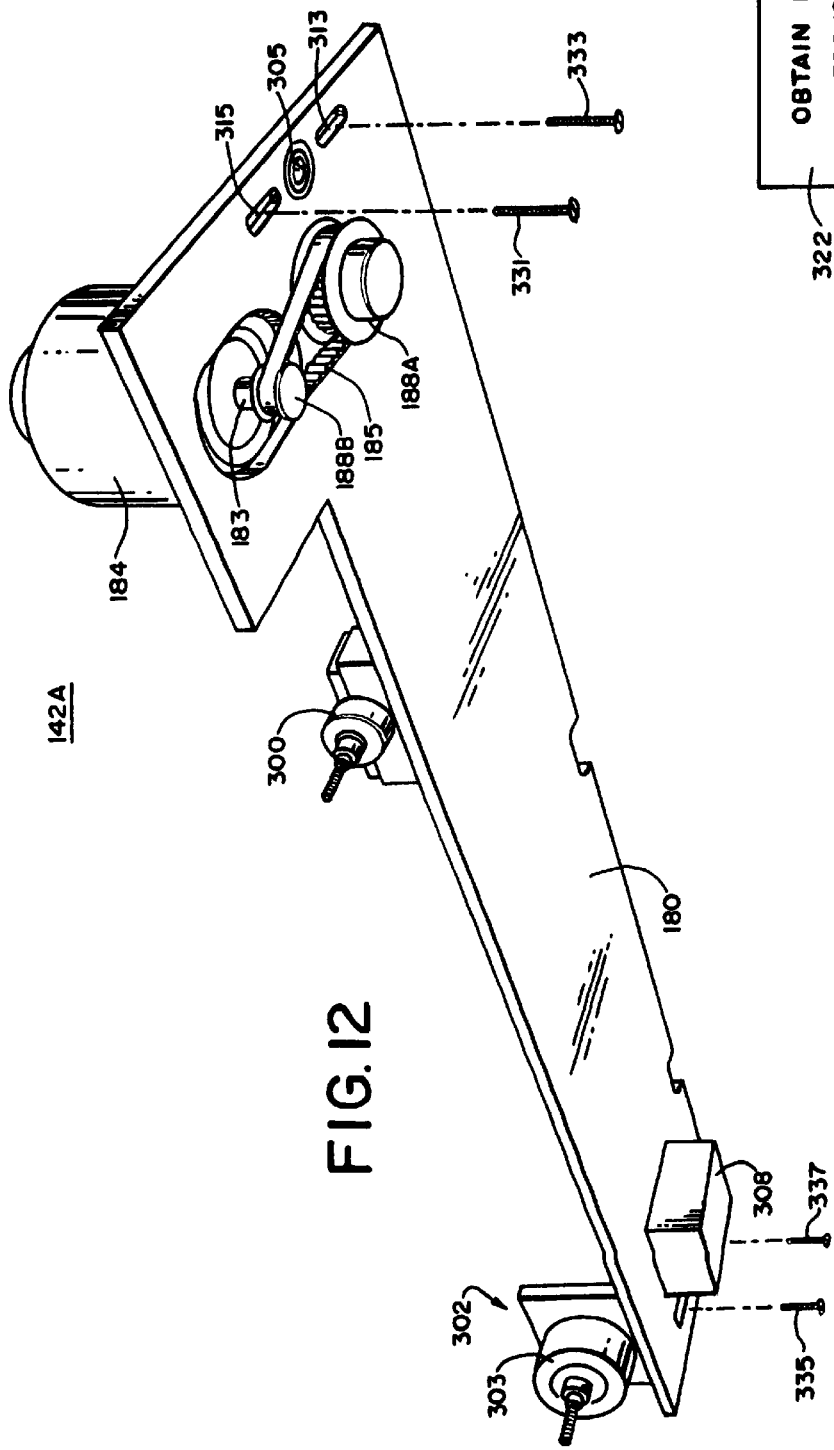
FIG. 12 is a perspective view from the bottom right side of the sequencing system of FIG. 11.

In FIG. 12, there is shown a bottom perspective view of the support plate 180 showing a mounting support means 308, shaft 183, pivot hole 305 and bolt holes 313 and 315, the motor assembly 184, the pivot and the pivot motor assembly 302 illustrating the manner in which the pivot pin is mounted to the frame to permit movement of the support plate 180 by the pivot motor assembly 302.

In the embodiment of FIGS. 11 and 12 the angle of the support plate 180 is changed to cause the microscope to remain focused during a scan. In another embodiment, the angle of the support plate 180 is not changed but the microscope is refocused at a number of points during a horizontal scan to maintain the focus point within the gel. This method has certain inertia problems which slow down the scan or decrease its precision because of the larger number of times the assembly must start or stop.

Figure 13:
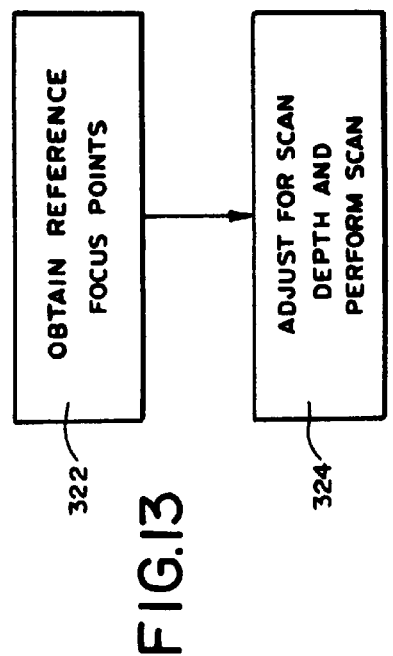
FIG. 13 is a flow diagram of a program used to control the operation of the system of FIG. 11 and FIG. 12.

In FIG. 13, there is shown a general block diagram 320 of a control program permitting the computer to control the focusing of the microscope during a scan so that the focal point remains within the gel of the gel sandwich. This program includes the general step 322 of obtaining focus points such as a single right and left point or a number of points and the step 324 of adjusting for scan depth and performing the scan.

In one embodiment, the focus points are in the gel away from the channels having DNA bands on both the right and left side of a horizontal scan and in another embodiment, it is at a plurality of points along a scan between channels having bands as well as near the ends of the scans. In another embodiment, the focusing is performed prior to the DNA bands being electrophoresed so that it is not necessary to select particular scan locations for the purpose of avoiding such DNA bands. In the former embodiment, the microscope is focused within the gel at one side, in which side there is the pivot point 305 (FIG. 11) in the scan support plate 180, and then at the second point. The microscope is moved to the second point without changing the scan. When the microscope is at the second point, the support plate 180 is moved so that, without adjusting the microscope further, the gel sandwich and support bed are altered in a parallel position. Then the microscope is refocused such that the focal point is within the gel for both locations, thus enabling a continuous scan thereafter which can proceed without dynamic focusing.

In the latter embodiment, as a scan is performed, the microscope assembly 172 refocuses at a number of points, preferably refocusing the lens by means of the focusing motor assembly, although the focusing could be done by adjusting the position of the support bed and gel sandwich with respect to each other or both focusing the lens and the position of the support bed and gel plate with respect to each other.

Figure 14:
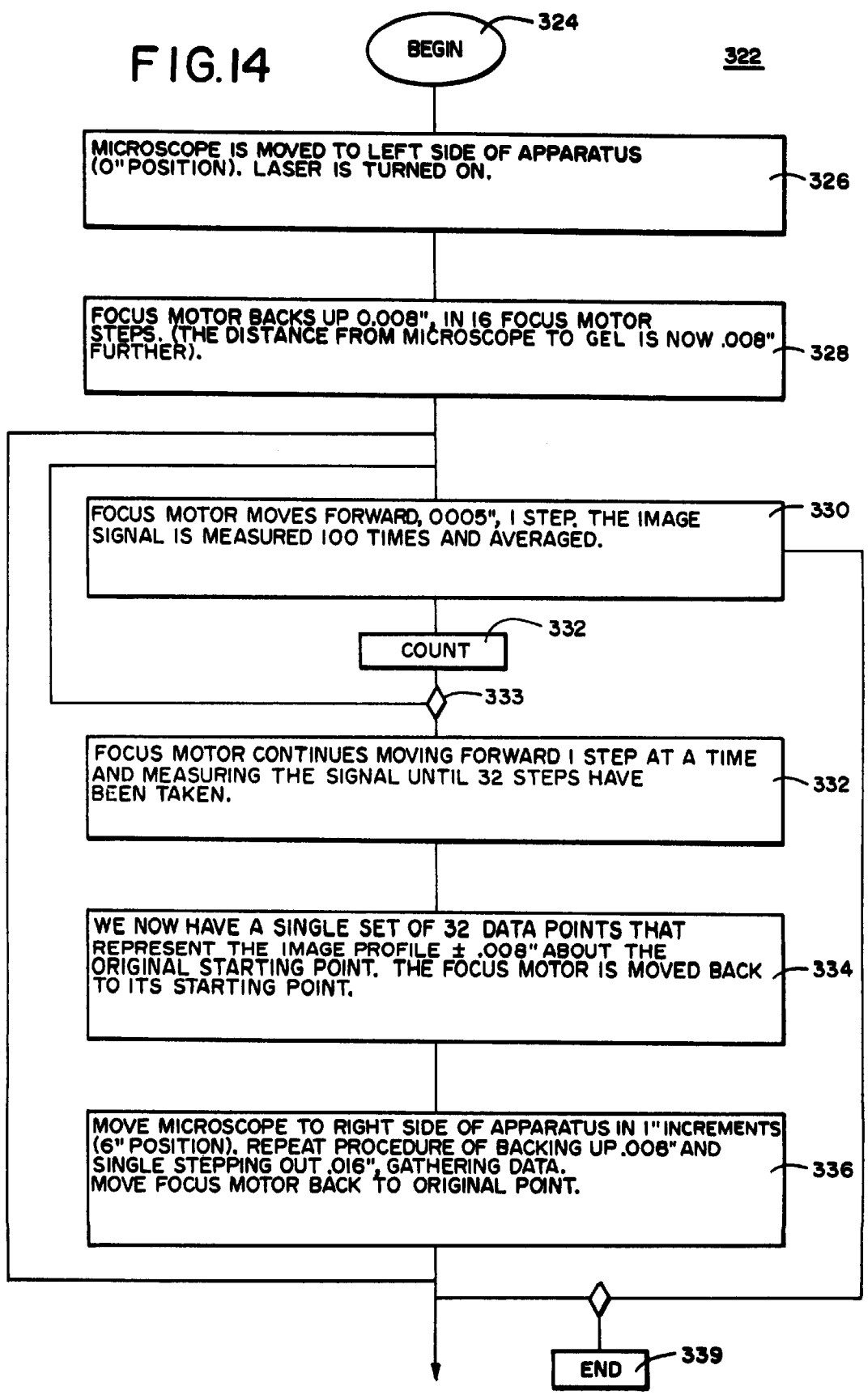
FIG. 14 is a more detailed flow diagram of the software control for a portion of the program of FIG. 13.

In FIG. 14, there is shown a block diagram of a subsequence of substeps within the step 322 for obtaining reference focal points including: (1) the substep 324 of beginning the program; (2) the substep 326 of moving the microscope to the left side of the apparatus (the zero position) and turning the laser on; (3) the substep 328 of backing the focus motor up 0.008 inches in 16 motor steps (the distance from microscope to gel is now 0.008 inches beyond the starting point at the gel sandwich); (4) the substep 330 of causing the focusing motor assembly to move forward one step, measuring the image signal one hundred times and obtaining the average of it; (5) the substep 332 of counting the steps the motor moves forward; (6) the substep 333 of deciding whether the count equals 32 motions forward or not, returning to the step 330 if it does not and if it does, the decision 332 to move to step 334; (7) the substep 334 of causing the focus motor to move back to its starting point; (8) the substep 336 of moving to a new position on the other side of the apparatus (right side in the preferred embodiment) at specified points such as one inch increments up to six inches along the scan and repeating steps 330 through 336 for each incremental location; and (9) followed by the decision step 336 of moving the scan back to its original zero point at end step 339.

With this arrangement, the microscope is moved to a starting point and focused at a number of locations for that particular starting point, such locations including the gel within them as well as portions of the glass supporting plates. Data is taken at each location a multiple number of times and averaged for precision, with this data being stored. The microscope is then moved in a horizontal scan operation to another point and the process repeated so that at least two data points are obtained and stored in the memory of the computer. These data points permit the position of the microscope and gel to be adjusted with respect to each other to maintain focus between them. It may be necessary to calculate the amount of pivoting of the microscope support and gel about a pivot point if a measurement is not directly at the pivot point.

In FIG. 15, there is shown a block diagram illustrating a subsequence within the step 324 (FIG. 13) of adjusting for scan depth and performing a scan including: (1) the substep 340 of determining where the minimum light emission occurred at different points; (2) the substep 342 of having the focus and pivot points moved so that the microscope is focused at the minimum fluorescence point at all of the locations; (3) the substep 344 of turning off the laser, moving the microscope to the zero position and resuming scanning with the laser turned back on if desired; and (4) the substep 346 of terminating the scan.

In FIG. 16, there is shown a block diagram of a program 350 illustrating a dynamic mode of scanning including: (1) the substep 352 of determining the minimum reading locations for left and right sides; (2) the substep 354 of determining the position along an equidistant straight line for at least eight points; (3) the substep 356 of moving the microscope to the zero position; (4) followed by the step 358 of scanning one section; (5) the step 360 of adjusting the focus again; (6) the step 362 of counting the adjustment; (7) the decision step 364 of determining if it is eight counts, and if not, returning to step 358 and repeating, and if it is, ending the scan; and (8) substep 366 of ending the dynamic focusing operation. With this arrangement, the microscope is refocused eight times in a scan operation.

In FIG. 17, there is shown a program 370 for controlling the scan comprising: (1) the step 372 of beginning the scan; (2) the step 374 in which the customer uses the host computer or scanner keyboard to start scanning; (3) the step 375 in which the scanner software initializes DMA (direct memory access) pointers and initializes a final position in the motor control integrated circuit; (4) the step 376 in which the scanning software tells the motor control integrated circuit to begin moving the microscope; (5) the step 378 in which a traverse of the microscope each 0.00048 inches causes the analog-to-digital converter to take one measurement and store that reading in memory; (6) the step 380 in which the scanner microprocessor is interrupted to say that a run is completed when the motor control integrated circuit is done moving a single one-way trip, either left or right; (7) the step 382 of processing data and sending it to the host computer while the motor is moving and taking data, (8) the decision step 384 to determine if scanning is to be continued, in which case the program returns to step 375 and if not, scanning is terminated at step 386; and (9) the step 386 of terminating the scan. As shown in this diagram, the computer control moves the scanner from place to place taking measurements along a path to perform a scanning operation.

Figure 18:
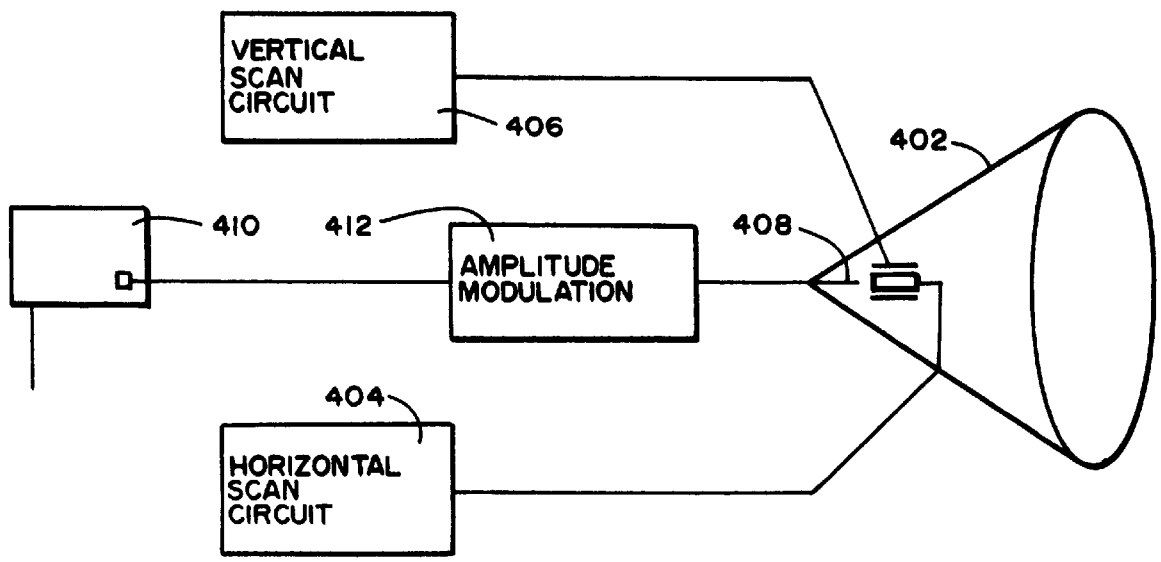
FIG. 18 is a schematic diagram of a display arrangement useful in the embodiment of FIGS. 1–17.
Figure 19:
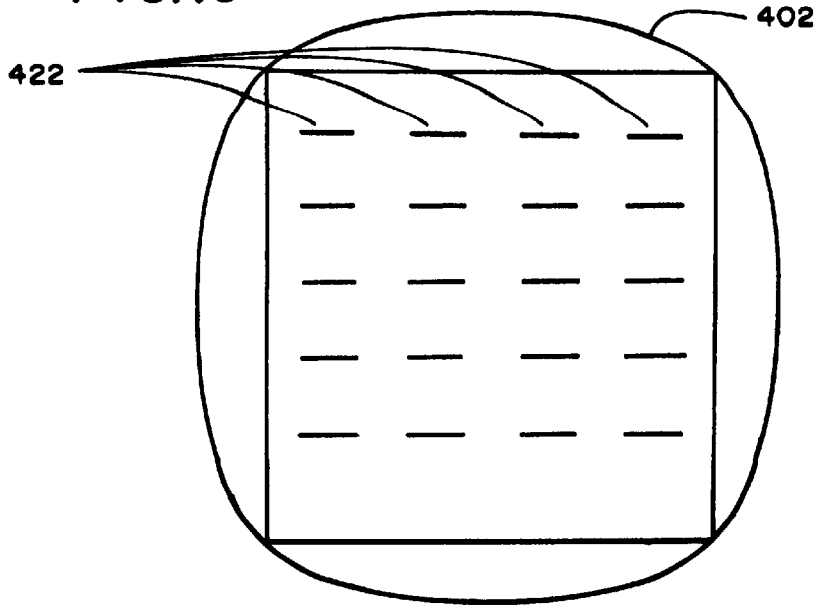
FIG. 19 is a front view of a display screen resulting from its use of the display arrangement of FIG. 18.

In FIG. 18, there is shown a block diagram of the display 400 having a cathode ray tube 402, a horizontal scan circuit 404, a vertical scan circuit 406, an electron gun 408, a driver 410 and an intensity control 412. As shown in this view, the horizontal scan control 404 periodically scans horizontally by applying a voltage to the deflection plates to move an electron beam from the gun 408 horizontally across the screen of the tube 402. At a less rapid rate, the vertical control 406 changes the vertical voltage to deflect the electron beam and form a raster. During the formation of the raster, data is applied to the driver 410 from the computer (FIG. 10) to modulate the voltage in the modulation control 412 to change the intensity corresponding to data. As shown in FIG. 19, the face of the cathode ray tube 402 scans across with its data to form a plurality of bands 422 in which the existence of markers is shown by a different intensity of light on the screen so that DNA channels in the gel are shown as dark and light bands in a manner similar to that shown by gel electrophoresis. With this arrangement, the scanning rate may be set to discriminate against noise, particularly discriminating against the natural fluorescense of the glass in the gel sandwich 150 (FIGS. 6 and 7). The screen display permits easy adjustment during measurements or data retrieval.

From the above summary, it can be understood that the sequencing techniques of this invention have several advantages, such as: (1) they take advantage of resolution over time, as opposed to space; (2) they are continuous; (3) they are automatic; (4) they are capable of sequencing or identifying markers in relatively long strands including strands of more than 100 bases; (5) they are relatively economical and easy to use; (6) they permit efficient focusing of a light sensor onto the DNA bands; (7) they provide an easy to observe display; (8) because the dyes have their emission spectra in the far red or near infrared light spectrum, small inexpensive far red or infrared laser diodes may be used; (9) the signal information is characterized by relatively low noise; and (10) they provide a simple protocol using universal termination of strands elongated by DNA polymerase.

While in the preferred embodiment, a single emission wavelength is used in the far red or near infrared region in each channel and for all of A, T, G and C terminated strands with the channel location identifying the terminating base type, multiple fluorescent markers can be used with the wavelength being used to identify the base type. In such an embodiment, an optical means detects a plurality of wavelengths and the computer correlates intensity data, corresponding lanes and corresponding wavelengths.

Although a preferred embodiment of the invention has been described with some particularity, many modifications and variations are possible in the preferred embodiment within the light of the above description. Accordingly, within the scope of the appended claims, the invention may be practiced other than as specifically described.

What is claimed is:

1. A method of DNA sequencing whereby DNA strands are used as templates to synthesize DNA fragments with limited synthesis, comprising the steps of using fluorescently marked A nucleotides to terminate synthesis at base type A, fluorescently marked G nucleotides to terminate synthesis at base type G, fluorescently marked C nucleotides to terminate synthesis at base type C, and fluorescently marked T nucleotides to terminate synthesis at base type T and analyzing the terminated DNA fragments so produced for the presence of fluorescent markers, thereby identifying the DNA sequence.

2. A process of DNA sequence analysis by chain elongation using terminators comprising reacting a template of DNA contained in an appropriate nucleotide, a primer, a polymerase, a first mixture of DNA nucleotides or their analogs, and a second mixture of terminators corresponding to the DNA nucleotides or their analogs, to produce fragments of DNA having terminators attached to a terminus introduced by chain termination events, wherein the terminators are fluorescently marked.

3. The process as set forth in claim 2 wherein the fragments of DNA having marked terminators attached to a terminus are analyzed for the presence of fluorescent markers, thereby identifying the DNA sequence.

* * * * *

UNITED STATES PATENT AND TRADEMARK OFFICE
CERTIFICATE OF CORRECTION

PATENT NO.   : 6,207,421 B1
DATED        : March 27, 2001
INVENTOR(S)  : Lyle Richard Middendorf and John A. Brumbaugh It is certified that error appears in the above-identified patent and that said Letters Patent is hereby corrected as shown below:

<u>Column 28,</u>
Line 27, change "contained in" to -- containing --.

Signed and Sealed this

Sixteenth Day of October, 2001

*Attest:*

NICHOLAS P. GODICI
*Attesting Officer*   *Acting Director of the United States Patent and Trademark Office*